(12) United States Patent
Bennaars-Eiden et al.

(10) Patent No.: US 11,629,371 B2
(45) Date of Patent: Apr. 18, 2023

(54) ARTICLE AND METHODS TO DETERMINE EFFICACY OF DISINFECTION PROCESS

(71) Applicant: 3M INNOVATIVE PROPERTIES COMPANY, St. Paul, MN (US)

(72) Inventors: Assumpta A. G. Bennaars-Eiden, Woodbury, MN (US); Tonya D. Bonilla, Woodbury, MN (US); Jodi L. Connell, St. Paul, MN (US); John J. Schmidt, Eagan, MN (US); Andrew W. Vail, Bayport, MN (US); Federica Sgolastra, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 964 days.

(21) Appl. No.: 16/475,258

(22) PCT Filed: Dec. 22, 2017

(86) PCT No.: PCT/US2017/068176
§ 371 (c)(1),
(2) Date: Jul. 1, 2019

(87) PCT Pub. No.: WO2018/125798
PCT Pub. Date: Jul. 5, 2018

(65) Prior Publication Data
US 2019/0338335 A1    Nov. 7, 2019

Related U.S. Application Data

(60) Provisional application No. 62/592,547, filed on Nov. 30, 2017, provisional application No. 62/474,108, (Continued)

(51) Int. Cl.
*G01N 15/06* (2006.01)
*C12Q 1/22* (2006.01)
(Continued)

(52) U.S. Cl.
CPC ............... *C12Q 1/22* (2013.01); *A47L 13/17* (2013.01); *A61L 2/00* (2013.01); *A61L 2/28* (2013.01);
(Continued)

(58) Field of Classification Search
CPC ..... A61L 2/26; A61L 2/28; C12M 1/34; C12Q 1/00
(Continued)

(56) References Cited

U.S. PATENT DOCUMENTS

| | | |
|---|---|---|
| 5,132,211 A | 7/1992 | Lundin |
| 6,261,811 B1 | 7/2001 | Hamdy |

(Continued)

FOREIGN PATENT DOCUMENTS

| | | |
|---|---|---|
| EP | 0699241 | 12/1998 |
| JP | 2007/007575 A | 1/2007 |

(Continued)

OTHER PUBLICATIONS

Extended European Search Report, EP1788742737, dated Nov. 11, 2018.
(Continued)

*Primary Examiner* — Monzer R Chorbaji
(74) *Attorney, Agent, or Firm* — Qiang Han

(57) ABSTRACT

An article is provided. The article comprises a nonwoven substrate having a copolymer grafted thereto, and a dried coating adhered to the substrate. The copolymer comprises interpolymerized monomer units of a quaternary ammonium-containing ligand monomer, an amide monomer, and an oxy monomer. The coating comprises a plurality of test microorganisms. Optionally, the coating further comprises a water-soluble or water-dispersible polymeric binding agent. A process challenge device comprising a body having a hollow channel with said article fixed disposed therein is
(Continued)

also provided. Methods of using the article or the process challenge device for determining the efficacy of a disinfection process are also provided.

16 Claims, 4 Drawing Sheets

Related U.S. Application Data filed on Mar. 21, 2017, provisional application No. 62/439,557, filed on Dec. 28, 2016.

(51) Int. Cl.
*A61L 2/28* (2006.01)
*C11D 17/04* (2006.01)
*A47L 13/17* (2006.01)
*A61L 2/00* (2006.01)
*D06M 14/26* (2006.01)
*D06M 14/00* (2006.01)
*A01N 47/44* (2006.01)

(52) U.S. Cl.
CPC ............ *C11D 17/049* (2013.01); *D06M 14/00* (2013.01); *D06M 14/26* (2013.01); *A01N 47/44* (2013.01)

(58) Field of Classification Search
USPC .......................................... 422/50, 420, 68.1
See application file for complete search history.

(56) References Cited

U.S. PATENT DOCUMENTS

| | | | |
|---|---|---|---|
| 6,352,837 B1 * | 3/2002 | Witcher | ................... A61L 2/28 435/31 |
| 6,566,090 B2 | 5/2003 | Witcher | |
| 7,569,359 B2 | 8/2009 | McDonnell | |
| 9,272,246 B2 | 3/2016 | Rasmussen | |
| 2003/0012688 A1 | 1/2003 | Kippenhan, Jr. | |
| 2015/0099413 A1 | 4/2015 | Berrigan | |
| 2016/0115430 A1 | 4/2016 | Swanson | |

FOREIGN PATENT DOCUMENTS

| | | |
|---|---|---|
| WO | WO 94/28164 | 12/1994 |
| WO | WO 2013-162695 | 10/2013 |
| WO | WO 2014-209798 | 12/2014 |
| WO | WO 2016-057520 | 4/2016 |
| WO | WO 2016-164329 | 10/2016 |
| WO | WO 2016-164439 | 10/2016 |
| WO | WO 2017-192305 | 11/2017 |
| WO | WO 2018-025207 | 2/2018 |
| WO | WO 2018-071618 | 4/2018 |

OTHER PUBLICATIONS

Arica, "Covalent Immobilization of Aspergillus Niger on pHEMA Membrane: Application to Continuous Flow Reactors", The Journal of Chemical Technology and Biotechnology, 1993, vol. 58, No. 3, pp. 281-285.

Garay-Flores, "Production of Glucose Oxidase and Catalase by Aspergillus Niger Free and Immobilized in Alginate-Polyvinyl Alcohol Beads", The Journal of General and Applied Microbiology, 2014, vol. 60, No. 6, pp. 262-269.

Sankalp, "Continuous Production of Gluconic Acid by Aspergillus Niger Immobilized on a Cellulosic Support: Study of Low pH Fermentative Behaviour of Aspergillus Niger", Process Biochemistry, Nov. 1999, vol. 35, No. 3-4, pp. 317-325.

Tokuda, "Hydrolysis of Xylan by Aspergillus Niger Immobilized on Non-woven fabrics", Bioscience Biotechnology and Biochemistry, Apr. 1997, vol. 61, No. 4, pp. 583-587.

Xue, "Antimicrobial Polymeric Materials with Quaternary Ammonium and Phosphonium Salts", International Journal of Molecular Sciences, Feb. 2015, vol. 16, No. 2, pp. 3626-3655.

International Search Report for PCT International Application No. PCT/US2017/068176, dated Feb. 20, 2018, 3 pages.

* cited by examiner

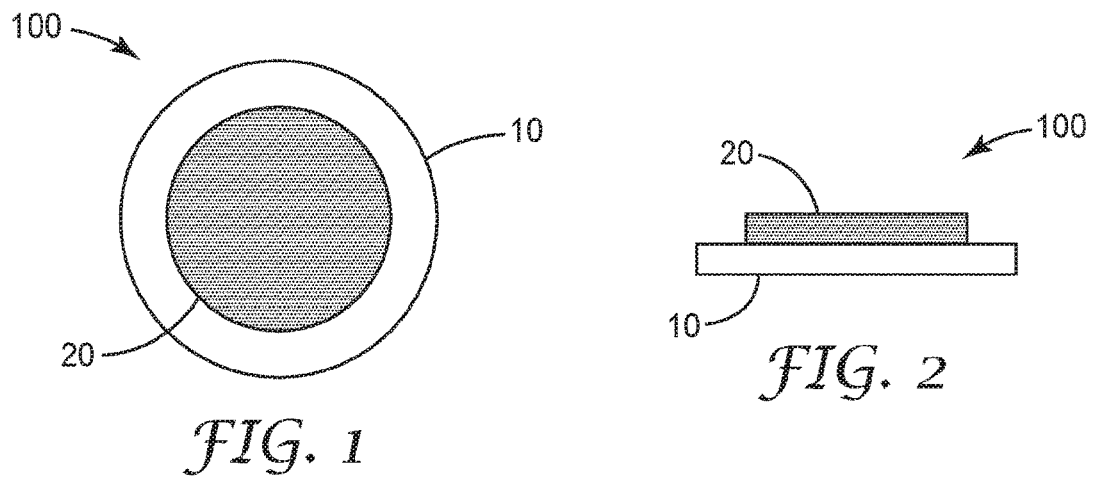
FIG. 1
FIG. 2
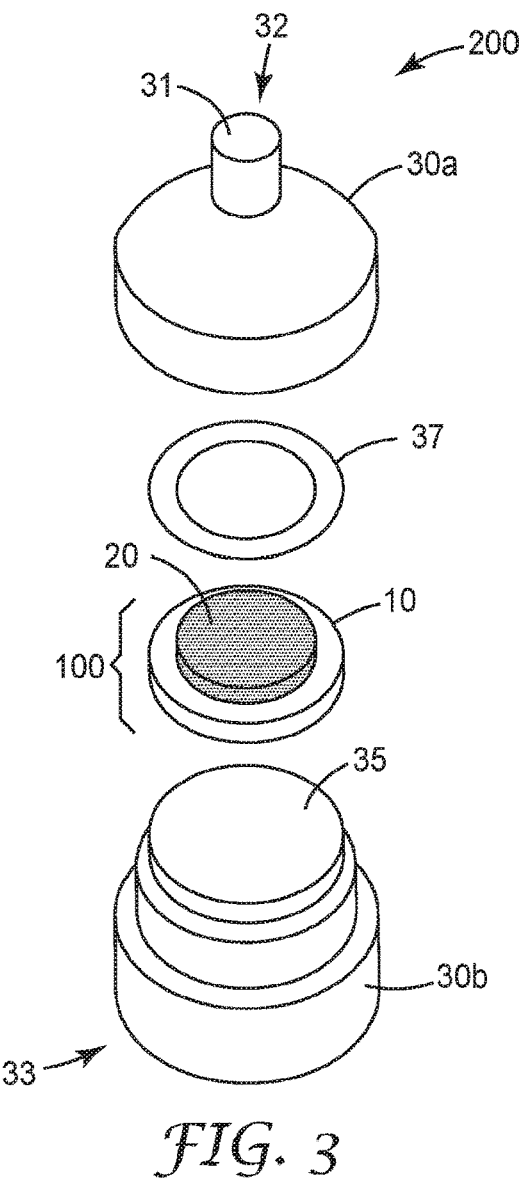
FIG. 3

ARTICLE AND METHODS TO DETERMINE EFFICACY OF DISINFECTION PROCESS

BACKGROUND

Endoscopic procedures play a beneficial role in the prevention, diagnosis and treatment of disease. Endoscopy procedures are performed using complex, reusable, flexible instruments that, when inserted into the hollow body, may become heavily contaminated with patient biomaterial and microorganisms, including potential pathogens. Careful reprocessing of flexible endoscopes between patients is critical to reducing the risk of cross-contamination and the possible transmission of pathogens.

Flexible endoscopes are rated as semi-critical according to the Spaulding classification for medical devices and therefore it is required that these devices be decontaminated by high-level disinfection. Thus, it is recommended that both endoscopes and reusable accessories be frequently visually inspected in the course of their use and reprocessing, including before, during and after use, as well as after cleaning and before high-level disinfection. However, a visually-based method of verification has severe limitations when applied to flexible endoscopes because the complex, narrow lumens in these devices cannot be directly visually inspected.

Automated endoscope reprocessors (AERs) are used to clean and disinfect flexible endoscopes to a level that mitigates transmission of pathogenic organisms and disease between patients who are subject to an endoscopic procedure. Typically, the only information available to a user is the parametric information provided by the AER equipment itself which consists primarily of time and temperature information. The AER does not monitor chemical parameters capable of establishing the effectiveness of the disinfection cycle. There is a need for improved biological indicators to monitor the efficacy of disinfection processes that use liquid disinfectants.

SUMMARY

The present disclosure generally relates to articles and devices for verifying the efficacy of a disinfection process. In particular, the present disclosure relates to methods and devices for verifying the efficacy of a disinfection process that contacts the items to be disinfected with a liquid disinfectant.

In one aspect, the present disclosure provides an article. The article can comprise a nonwoven substrate and a dried coating adhered to the substrate. The nonwoven substrate can have a copolymer grafted thereto. The copolymer can comprise interpolymerized monomer units of a cationic nitrogen-containing ligand monomer selected from quaternary ammonium-containing and/or guanidinyl-containing ligand monomers, an amide monomer, and an oxy monomer. The dried coating can comprise a plurality of test microorganisms.

In any of the above embodiments, the grafted copolymer can comprise a) 10 to 50 parts by weight of the cationic nitrogen-containing ligand monomer, b) 10 to 80 parts by weight of the amide monomer, c) 10 to 40 parts by weight of the oxy monomer, and 0 to 30 parts by weight of a poly(alkylene oxide) monomer, wherein a sum of a) to d) is 100 parts by weight. In any of the above embodiments of the article, the dried coating can further comprise a water-soluble or water-dispersible polymeric binding agent. In any of the above embodiments, the nonwoven substrate can comprise meltblown microfibers of a hydrophobic thermoplastic polyolefin. In any of the above embodiments, the article can have a weight ratio of copolymer to nonwoven substrate, wherein the weight ratio is about 0.5 to 3 parts copolymer to 1 part nonwoven substrate.

In any of the above embodiments, the test microorganisms comprise spores. In any of the above embodiments, the spores can comprise spores of a species of filamentous fungi. In any of the above embodiments, the spores can comprise spores of *Aspergillus brasiliensis*, *Aspergillus oryzae*, *Aspergillus niger*, or *Aspergillus nidulans*. In some embodiments, the test microorganisms can comprise *Geobacillus stearothermophilus* and *Bacillus atrophaeus* (formerly known as *Bacillus subtilis*).

In any of the above embodiments, the quaternary ammonium-containing monomer used to make the copolymer can comprise [3-(Methacryloylamino)propyl]trimethylammonium chloride. In any of the above embodiments, the quaternary ammonium-containing monomer used to make the copolymer can comprise [3-(Methacryloylamino)propyl]trimethylammonium chloride, the oxy monomer used to make the copolymer can comprise glycidyl methacrylate, and the amide monomer used to make the copolymer can comprise N-vinyl pyrrolidone.

In another aspect, the present disclosure provides a process challenge device. The process challenge device can comprise a body with a hollow channel having a first aperture and a second aperture spaced apart from the first aperture, and an article fixedly disposed in the hollow channel. The article can comprise a nonwoven substrate and a dried coating adhered to the substrate. The nonwoven substrate can have a copolymer grafted thereto. The copolymer can comprise interpolymerized monomer units of a cationic nitrogen-containing ligand monomer selected from quaternary ammonium-containing and/or guanidinyl-containing ligand monomers, an amide monomer, and an oxy monomer. The dried coating can comprise a plurality of test microorganisms and an optional water-soluble or water-dispersible polymeric binding agent.

In any of the above embodiments, the process challenge device further can comprise a reservoir containing a detection medium. The reservoir can be disposed in selective fluid communication with the article. In some embodiments, the detection medium can comprise a reagent selected from the group consisting of an effective amount of a nutrient that facilitates germination and/or growth of the test microorganisms, an indicator compound facilitates detection of a test microorganism metabolic activity, an effective amount of a neutralizer compound that inhibits an antimicrobial activity of a disinfectant, and a combination of any two or more of the foregoing reagents.

In any of the above embodiments, the body of the process challenge device comprises a wall that forms the hollow channel, wherein a portion of a wall permits optical evaluation of the test microorganisms or a product of metabolic activity of the test microorganisms.

In yet another aspect, the present disclosure provides a first method. The method can comprise flowing a disinfectant through the hollow channel of any of the above embodiments of the process challenge device, wherein the process challenge device comprises a reservoir containing the detection medium, wherein the detection medium comprises the effective amount of the nutrient and the indicator compound, wherein flowing the disinfectant through the hollow channel comprises contacting the article with the disinfectant. The first method further can comprise: while flowing the disinfectant through the hollow channel and/or after flowing the disinfectant through the hollow channel, contacting the article with the disinfectant in the hollow channel at a predefined temperature for at least a predetermined minimum contact time; after contacting the article with the disinfectant for at least the predetermined minimum contact time, contacting the article with an effective amount of a neutralizer compound that inhibits an antimicrobial activity of the disinfectant; contacting the article with the detection medium in the hollow channel for a period of time; and after contacting the article with the detection medium in the hollow channel for the period of time, analyzing the detection medium in the hollow channel to determine whether the indicator compound changed from a first state to a second state.

In yet another aspect, the present disclosure provides a second method. The method can comprise contacting an article with a disinfectant in a flow stream for at least a predefined minimum contact time. The article can comprise a nonwoven substrate and a dried coating adhered to the substrate. The nonwoven substrate can have a copolymer grafted thereto. The copolymer can comprise interpolymerized monomer units of a cationic nitrogen-containing ligand monomer selected from quaternary ammonium-containing and/or guanidinyl-containing ligand monomers, an amide monomer, and an oxy monomer. The dried coating can comprise a plurality of test microorganisms and an optional water-soluble or water-dispersible polymeric binding agent. The second method further can comprise: after contacting the article with the disinfectant for at least the minimum contact time, contacting the article with an effective amount of a neutralizer compound that inhibits an antimicrobial activity of the disinfectant; contacting the article with a detection medium for a period of time; and after contacting the article with the detection medium for a period of time, analyzing the detection medium to detect a biological activity of the test microorganisms.

In any of the above embodiments of the first method or the second method, the minimum contact period can be about 3 minutes to about 90 minutes. In any of the above embodiments of the first method or the second method, contacting the article with the detection medium for a period of time comprises contacting the article with the detection medium for about 5 minutes to about 48 hours.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, "a" nonwoven substrate can be interpreted to mean "one or more" nonwoven substrates.

The term "and/or" means one or all of the listed elements or a combination of any two or more of the listed elements.

"Hydrocarbyl", as used herein, is inclusive of aryl and alkyl;

"(Hetero)hydrocarbyl", as used herein, is inclusive of hydrocarbyl alkyl and aryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

"(Hetero)arylene", as used herein, is inclusive of arylene and heteroarylene.

"Outgrowth", as used herein, refers to the biological process of growth and/or reproduction of a vegetative cell including, for example, a vegetative cell that is formed by the germination of a spore.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The Figures and the detailed description which follow more particularly exemplify illustrative embodiments. Other features, objects and advantages will become apparent from the description and drawings, and from the claims.

BRIEF DESCRIPTION OF DRAWINGS

FIG. 1 is a plan view of one embodiment of an article according to the present disclosure.

FIG. 2 is a side view of the article of FIG. 1.

FIG. 3 is a perspective side view of one embodiment of a process challenge device according to the present disclosure.

DETAILED DESCRIPTION

Figure 4:
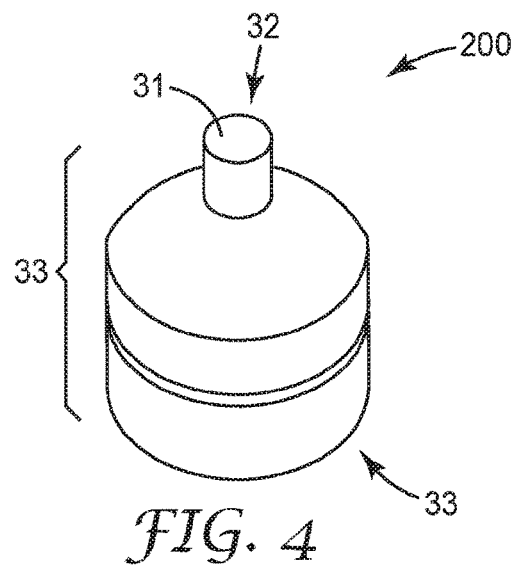
FIG. 4 is an exploded view of the process challenge device of FIG. 3.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to articles, devices, and methods that may be used to verify the efficacy of a disinfection or sterilization process. In particular, the present disclosure relates to an article comprising a nonwoven carrier with a composition of microorganisms disposed in a polymer matrix coated thereon. Advantageously, the article can be immersed in a liquid (e.g., a flowing aqueous liquid wherein the liquid flows by and/or through the article) for a period of time without substantial release of the microorganisms from the article. Accordingly, the article can be used to validate a disinfection process that uses a liquid flow stream of disinfectant (e.g., a process for cleaning and disinfecting endoscopes).

In one aspect, the present disclosure provides an article. FIGS. 1 and 2 show various views of one embodiment of an article 100 according to the present disclosure. The article 100 comprises a substrate 10 and a dried coating 20 adhered to the substrate. In any embodiment, the substrate 10 can be a sheet-like material. An example of a suitable sheet-like material for the substrate 10 is a nonwoven fabric such as, for example, a nonwoven fabric comprising meltblown fibers (e.g., meltblown fibers of a hydrophobic thermoplastic olefin).

In any embodiment wherein the substrate is a nonwoven substrate, the nonwoven substrate has a surface area of about of 15 to 50 m² per square meter of nonwoven substrate. In any embodiment wherein the substrate is a nonwoven substrate, the nonwoven substrate has a solidity of less than 20%.

In any embodiment wherein the substrate is a nonwoven substrate comprising meltblown microfibers, the substrate can have a copolymer (not shown) grafted thereto. The copolymer can comprise interpolymerized monomer units of a cationic nitrogen-containing ligand monomer selected from quaternary ammonium-containing and/or guanidinyl-containing ligand monomers, an amide monomer, and an oxy monomer. Suitable nonwoven polymers having a copolymer grafted thereto are described in International Publication No. WO 2013/162695 entitled "Nonwoven Article Gafter with Copolymer", which is incorporated herein by reference in its entirety. Suitable monomer units for producing the grafted copolymers used to make the article of the present disclosure are also described in International Publication No. WO 2013/162695

In any embodiment, the grafted copolymer can comprise about 10 to 50 parts by weight of the cationic nitrogen-containing ligand monomer, about 10 to 80 parts by weight of the amide monomer, and about 10 to 40 parts by weight of the oxy monomer. Optionally, the grafted copolymer can comprise about 0 to 30 parts by weight of a poly(alkylene oxide) monomer. The sum of the portions of each of the aforementioned monomers is 100 parts by weight. In any embodiment, the weight of the grafted polymer can be 0.5 to 5 times the weight of the nonwoven substrate. In any embodiment wherein the polymer comprises poly(alkylene oxide), wherein the poly(alkylene oxide) has a weight average molecular weight of 20,000 Daltons.

The polymer grafted article comprises a nonwoven substrate, and a grafted copolymer comprising interpolymerized monomer units of a) a cationic nitrogen-containing ligand monomer; b) an amide monomer, and c) an "oxy" monomer. The cationic nitrogen-containing ligand monomer includes quaternary ammonium-containing ligand monomers and guanidinyl-containing ligand monomers. The "oxy" monomer is inclusive of epoxy monomers and $C_3$-$C_{10}$, preferably $C_4$-$C_6$, monoether-containing monomers. More specifically, the grafted copolymer comprises interpolymerized monomer units including a. 10 to 50 parts by weight of the cationic nitrogen-containing ligand monomer;

b. 10 to 80 parts by weight of the amide monomer, and c. 10 to 40 parts by weight of the oxy monomer; and wherein the sum of a to c is 100 parts by weight.

The cationic nitrogen-containing ligand monomer is of the general formula:

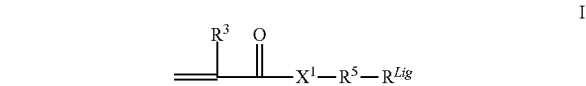

I where $X^1$ is —O— or —$NR^3$—, $R^3$ is H or $C_1$-$C_4$ alkyl-; $R^5$ is an (hetero)hydrocarbyl group, preferably a hydrocarbyl group, more preferably a $C_1$-$C_8$ alkylene, and $R^{Lig}$ is a quaternary ammonium ligand group or a guanidinyl-containing ligand group.

In any embodiment, the cationic nitrogen-containing ligand monomer is a quaternary ammonium monomer is of the general formula:

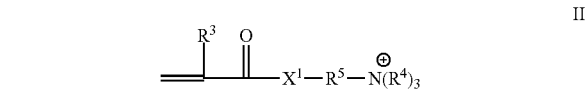

II where $X^1$ is —O— or —$NR^3$—, where each $R^3$ is H or $C_1$-$C_4$ alkyl, preferably H or methyl; and $R^5$ is an alkylene (e.g., an alkylene having 1 to 10 carbon atoms, 1 to 6, or 1 to 4 carbon atoms), each $R^4$ is independently hydrogen, alkyl, or aryl.) and may be substituted by a hydroxyl group. The counter ions of the quaternary ammonium salts are often halides, sulfates, phosphates, nitrates, and the like. Such monomers having a quaternary ammonium group preferably may be directly grafted to the surface of the nonwoven substrate (in the presence of the additional co-monomers described herein), or less preferably an aminoalkyl (meth)acryloyl monomer having a primary, secondary or tertiary amine group, may be grafted and subsequently converted by alkylation to a quaternary ammonium group of Formula II.

Useful aminoalkyl (meth)acrylates (i.e., in Formula II is oxy) include trialkylaminoalkyl(meth)acrylates such as, for example, trimethylaminoethylmethacrylate, trimethylaminoethylacrylate, triethylaminoethylmethacylate, triethylaminoethylacrylate, trimethylaminopropylmethacrylate, trimethylaminopropylacrylate, dimethylbutylaminopropylmethacrylate, diethylbutylaminopropylacrylate and the like.

Exemplary amino (meth)acrylamides (i.e., $X^1$ in Formula II is —$NR^3$—) include, for example, 3-(trimethylamino)

propylmethacrylamide, 3-(triethylamino)propylmethacrylamide, 3-(ethyldimethylamino)propylmethacrylamide.

Suitable quaternary salts of the aminoalkyl (meth)acryloyl monomers of Formula I include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

The grafted copolymer may comprise 10 to 50 parts by weight, preferably 20 to 40 parts by weight, of such quaternary amine monomer units, relative to 100 parts total grafting monomer(s).

In some embodiment the grafted copolymer comprises cationic guanidinyl-containing ligand monomers of the Formula IIIa or b. Such compounds may contain agmatine-containing ligands; guanidine and biguanide containing ligands.

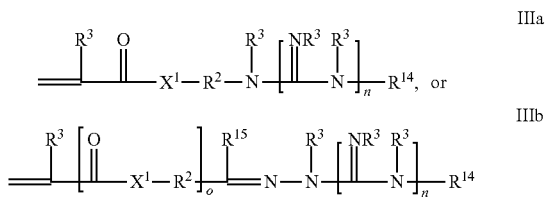

wherein
$R^2$ is a (hetero)hydrocarbyl group, preferably a divalent alkylene having 1 to 10 carbon atoms;
each $R^3$ is independently H or hydrocarbyl, preferably $C_1$-$C_4$ alkyl;
$R^{14}$ is H, $C_1$-$C_4$ alkyl or —$N(R^3)_2$;
$R^{15}$ is H or hydrocarbyl, preferably $C_1$-$C_4$ alkyl or aryl;
$X^1$ is —O— or —$NR^3$—,
o is 0 or 1, and
n is 1 or 2.

Such ligand monomers may be made by condensation of an alkenyl or alkenoyl compound, typically a (meth)acryloyl halide, a (meth)acryloylisocyanate, or an alkenylazlactone, with a compound of formulas IVa or IVb:

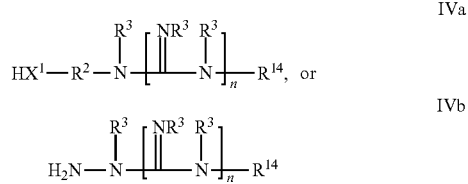

where $X^1$, and $R^2R^3$, $R^{14}$, $R^{15}$, and n are as previously defined.

Other ligand monomers may be made by condensation of a carbonyl containing monomer, such as acrolein, vinylmethylketone, diacetone acrylamide or acetoacetoxyethylmethacrylate, with a compound of formulas IVa or IVb.

The grafted copolymer may comprise 10 to 50 parts by weight, preferably 20 to 40 parts by weight, of such cationic guanidinyl-containing ligand monomers units, relative to 100 parts total grafting monomer(s). The cationic nitrogen-containing ligand monomer may comprise quaternary amine monomer units of Formula II, guanidinyl-containing monomer units of formulas IIIa or b, or a mixture of both such monomer units.

The grafted copolymer further comprises "oxy monomer" units which are inclusive of epoxy functional monomer units and alkyl ether functional monomer units. Desirably, the oxy monomers have an aqueous solubility of 15-25 g/L. Such "oxy monomer" include epoxy-functional and monoether-functional (meth)acrylates and (meth)acrylamides and include those of the general formula:

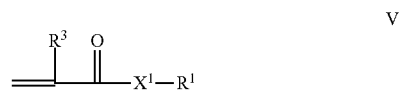

wherein:
$R^3$ is —H or $C_1$-$C_4$ alkyl;
$X^1$ is —$NR^3$— or —O—; and
$R^1$ is an epoxy-functional or ether-functional (hetero)hydrocarbyl group. More particularly the ether functional group is a lower alkyleneoxy alkyl group. Preferably, the $R^1$ group is based on a straight-chain, branched, cyclic or polycyclic hydrocarbon of 2 to 30 carbons having an oxirane (epoxy) group included. More preferably, the $R^8$ group contains 3 to 10 carbons, such as glycidyl methacrylate (GMA).

Some preferred epoxy monomers are of the formula:

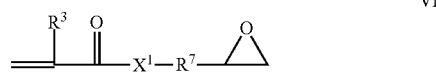

wherein:
$R^7$ is a (hetero)hydrocarbyl group, preferably a hydrocarbyl group, more preferably a $C_1$-$C_6$ alkylene;
$R^3$ is —H or $C_1$-$C_4$ alkyl; and
$X^1$ is —$NR^3$— or —O—.

Representative epoxy monomers include glycidyl (meth)acrylate, thioglycidyl (meth)acrylate, 3-(2,3-epoxypropoxy)phenyl (meth)acrylate, 2-[4-(2,3-epoxypropoxy)phenyl]-2-(4-(meth)acryloyloxyphenyl)propane, 4-(2,3-epoxypropoxy)cyclohexyl (meth)acrylate, 2,3-epoxycyclohexyl (meth)acrylate, and 3,4-epoxycyclohexyl (meth)acrylate.

In one useful embodiment, the epoxy functional monomer is derived from the reaction of vinyldimethyl azlactone with a hydroxyalkyl epoxy compound as shown in Scheme 1:

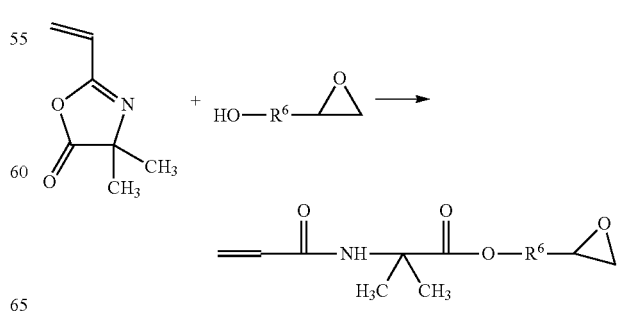

where $R^6$ is a $C_1$-$C_6$ alkylene.

It is believed that the epoxy groups of these monomers in the grafted copolymer hydrolytically ring open to provide terminal, pendent diol groups on the copolymer. Thus the original grafted hydrophobic epoxy group hydrolyzes to provide a hydrophilic diol group to the grafted copolymer.

The "oxy monomers" alternatively may be selected from lower alkyl ether functional monomers. Such ether functional monomers comprise lower monomer ether monomers of the formula:

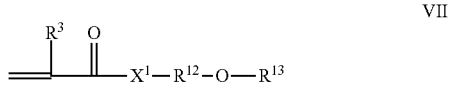

VII where
$R^3$ is —H or $C_1$-$C_4$ alkyl; and
$X^1$ is —$NR^3$— or —O—,
$R^{12}$ is a linear or branched $C_2$-$C_4$ alkylene, and
$R^{13}$ is a linear or branched $C_1$-$C_4$ alkyl. Preferably the sum of the carbon atoms of the $R^{12}$ and $R^{13}$ groups is from 3 to 10, preferably 3 to 6.

The grafted copolymer may comprise 10 to 40 parts by weight, preferably 15 to 35 parts by weight, of such oxy monomer units, relative to 100 parts total grafting monomer(s).

The grafted polymer optionally contains other ethylenically-unsaturated hydrophilic amide monomer units. As used herein these "hydrophilic monomers" are those polymerizable amide monomers having a water miscibility (water in monomer) of at least 1 wt. %, preferably at least 5 weight % without reaching a cloud point. The hydrophilic amide monomer units include (meth)acrylamides and N-vinyl amides are of the general formulas:

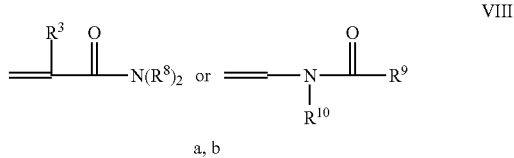

VIII where
$R^3$ is —H or $C_1$-$C_4$ alkyl;
Each $R^8$ is an H, an alkyl or an aryl group,
$R^9$ and $R^{10}$ are alkyl groups, or may be taken together to form a 5 or 6-membered ring.

Examples of suitable hydrophilic monomers include N-vinyl caprolactam, N-vinyl acetamide, N-vinyl pyrrolidone, acrylamide, mono- or di-N-alkyl substituted acrylamide, and combinations thereof. Preferred polar monomers include N-vinyl pyrrolidone, N-vinyl acetamide, methylacrylamide, and mixtures thereof.

The grafted copolymer may comprise 10 to 80 parts by weight, preferably 30 to 60 parts by weight, of such amide monomer units, relative to 100 parts total grafting monomer(s).

In some preferred embodiments, the quaternary ammonium-containing monomer used to make the copolymer comprises [3-(Methacryloylamino)propyl]trimethylammonium chloride (MAPTAC). In some preferred embodiments, the oxy monomer used to make the copolymer comprises glycidyl methacrylate. In some preferred embodiments, the amide monomer used to make the copolymer comprises N-vinyl pyrrolidone. In a preferred embodiment, the quaternary ammonium-containing monomer used to make the copolymer comprises [3-(Methacryloylamino)propyl]trimethylammonium chloride, the oxy monomer used to make the copolymer comprises glycidyl methacrylate, and the amide monomer used to make the copolymer comprises N-vinyl pyrrolidone.

In any embodiment, the quaternary ammonium-containing monomer and the oxy monomer used to make the copolymer each comprises a monomer selected from the group consisting of an acrylate monomer, a methacrylate monomer, an acrylamide monomer, and a methacrylamide monomer. In any of these embodiments, the amide monomer is selected from the group consisting of an acrylamide monomer, a methacrylamide monomer, and an N-vinylamide monomer.

In any embodiment, the oxy monomer used to make the copolymer comprises a monomer selected from the group consisting of an acrylate monomer, a methacrylate monomer, an acrylamide monomer, and a methacrylamide monomer with an epoxy substituent.

With regard to the grafting monomers supra, the monomers that are grafted to the surface of the nonwoven substrates usually will have either an acrylate or other non-acrylate polymerizable functional group for grafting by e-beam. Methacryloyl groups are preferred for grafting of the monomer to the nonwoven substrate surface (using the process described herein) due to the slower, more uniform reactivity and durability of such methacryloyl monomers to nonwovens that have been exposed to e-beam irradiation.

In any embodiment, the cationic nitrogen-containing ligand monomer can be an inorganic acid or organic acid salt, such as for example a hydrochloride salt, phosphate salt, sulfate salt, hemisulfate salt, nitrate salt, acetate salt, mesylate salt, tosylate salt, tartrate salt, hemitartrate salt, or benzoate salt.

The dried coating 20 comprises a plurality of test microorganisms (e.g., bacteria, spores). The test microorganisms (e.g., bacteria, spores) comprise, and/or are capable of producing, a detectable biological activity (e.g., an enzyme activity). In any embodiment, the detectable biological activity, or the ability of the test microorganisms to produce the detectable biological activity, can be annihilated by exposing (e.g., by contact) the test microorganisms to a disinfection process that is effective to kill the microorganisms. In any embodiment wherein the test microorganisms are spores, the spores in the dried coating 20 can be viable spores (i.e., capable of biological activities such as germination and/or binary fission (after germination)).

Optionally, the dried coating 20 adhered to the substrate 10 further comprises water-soluble or water-dispersible polymer capable of acting as a binding agent (for the microorganisms). The polymeric binding agent serves to minimize the removal of the microorganisms from the article during the disinfection process. Preferably, the polymeric binding agent, once dried, is slow to re-dissolve in an aqueous buffer or aqueous disinfection solution. The rate of dissolution can be controlled by a number of factors. For example, increasing the molecular weight of the polymeric binding agent results in a decrease in the rate of dissolution. A preferred way of controlling dissolution rate is to use a hydrophilic polymeric binding agent that is capable of forming a hydrogel. A hydrogel can be formed from a polymer solution, for example, by a temperature change or upon dry down. The hydrogel is produced, for example, as a result of the formation of hydrogen bonds, or by crystallization, or by other polymer-polymer interactions.

The suitability of a potential polymeric binding agent is easily tested by measuring microorganism wash off in the presence of the polymeric binding agent compared to the wash-off of the test microorganisms in the absence of the polymeric binding agent, as shown herein.

Suitable examples of polymers useful as binding agents include natural and synthetic, ionic and nonionic polymers and copolymers. Typical polymers include those used as coatings or binders for modified or controlled release of pharmaceutical ingredients such as, for example, modified cellulosic polymers, including among others methylcellulose, ethylcellulose, hydroxypropylcellulose, and hydroxyethylcellulose. Others include polyvinylpyrrolidone, polyethylene oxide, and polypropylene oxide. Typical polymers known to form hydrogels include, among others, agarose, methylcellulose, hyaluronic acid, gelatin, guar, polyvinyl alcohol, and neutralized or partially neutralized polyacrylic acid. Anionic polymers, including polymers such as hyaluronic acid, polyacrylic acid and copolymers, polyAMPS, and dextran sulfate, are useful binders since they also provide ionic interaction with the grafted substrate, thus decreasing the rate of re-dissolution.

When producing an article according to the present disclosure, the optional hydrophilic polymer can be hydrated with an aqueous solvent (e.g., water, an aqueous buffer) and the test microorganisms can be suspended (e.g., uniformly suspended) in the resulting hydrogel. Alternatively, the test microorganisms can be suspended in a suitable suspending liquid (e.g., water, a buffered aqueous solution). The concentration of test microorganisms in the suspending liquid or the hydrogel can be adjusted so that applying a predetermined volume of the hydrogel to the substrate results in the delivery of a predetermined number of test microorganisms onto the substrate. The predetermined number of viable test microorganisms on the article can be about 10 test microorganisms, about 100 test microorganisms, about $10^3$ test microorganisms, about $10^4$ test microorganisms, about $10^5$ test microorganisms, about $10^6$ test microorganisms, about $10^7$ test microorganisms or about $10^8$ test microorganisms.

After suspending the test microorganisms (e.g., spores) in the suspending liquid or the hydrogel, the predetermined volume of suspending liquid or hydrogel can be deposited (e.g., by pipet) onto the substrate and the liquid coating can be dried to produce a dried coating that is essentially water-free. Before and during the drying step, the coating can migrate into voids in the surface of the substrate.

The liquid coating can be dried under room temperature conditions or in some cases by using mild heating.

Advantageously, dispersing the test microorganisms in the dried polymeric binding agent, when present, provides a matrix in which the test microorganisms are trapped when the article is placed into a liquid disinfectant (e.g., an aqueous disinfectant). Thus, if the article is fixedly disposed in a device through which the liquid disinfectant flows, the polymeric binding agent matrix minimizes or prevents migration of the test microorganisms from the device into the bulk liquid flow stream of the disinfectant.

The test microorganisms can be any suitable test microorganisms for testing the efficacy of a disinfection process. Suitable test microorganisms include bacteria (e.g., a species of the genus *Mycobacterium*) bacterial spores and fungal spores that are known in the art. In any embodiment wherein the test microorganisms are spores, the spores used in the coating 20 can comprise spores of a species of filamentous fungi or bacteria bacterial spores. In any embodiment, the spores of the filamentous fungi can comprise spores of a species of *Aspergillus*. In any embodiment, the spores of a species of *Aspergillus* can comprise spores of *Aspergillus brasiliensis, Aspergillus oryzae, Aspergillus niger*, or *Aspergillus nidulans*, for example. In any embodiment, bacteria bacterial spores can comprises the spores of a species of *Geobacillus*. In any embodiment, the spores of a species *Geobacillus* can comprise spores of *Geobacillus stearothermophilus.* process and/or equipment to be tested. In any embodiment, the substrate 10 can be dimensioned to be placed into, for example, a flow channel (e.g., a hollow tube such as an endoscope, e.g.; not shown) through which the disinfectant is directed during the disinfection process. Alternatively, the substrate 10 can be dimensioned to be placed into a process challenge device that is placed into, or connected to, the flow channel. The substrate 10 can comprise a sheet-like material, as discussed herein. In any embodiment, the substrate 10 can have a surface area of about 4 $mm^2$ to about 1600 $mm^2$. In any embodiment, the substrate 10 can be shaped in the form of a circle, an oval, or a polygon (e.g., a square, a rectangle, a rhombus, a pentagon, a hexagon, an octagon), for example. In use, the substrate 10 may be rolled or folded prior to placement of the substrate into a process challenge device and/or placement into a flow stream of a disinfectant.

In another aspect, the present disclosure provides a process challenge device. FIGS. 3 and 4 show various views of one embodiment of a process challenge device 200 according to the present disclosure. The illustrated embodiment of process challenge device 200 resembles a SWINNEX™ filter holder with the article 100 described hereinabove contained therein. The process challenge device 200 comprises a body 30 with a first aperture 31, a second aperture 33 spaced apart from the first aperture, and a hollow channel 32 extending through the body from the first aperture to the second aperture. The process challenge device 200 further comprises an article 100 fixedly disposed in the hollow channel 32 of the body. The article 100 is any embodiment of the article comprising a substrate and a dried coating comprising a polymeric binding agent and a plurality of test microorganisms according to the present disclosure.

"Fixedly disposed", as used herein, refers to the condition wherein the article (e.g., article 100) is retained in the hollow channel (e.g., hollow channel 32) via an attachment means (e.g., a clamp, an adhesive) and/or by entrapment of the article in the hollow channel, for example. The article is retained such that a fluid (e.g., a disinfectant) passing through the hollow channel contacts and/or passes through the article without expelling the article from the hollow channel "Fixedly disposed" does not necessarily mean the article is permanently disposed in the hollow channel. In some embodiments, the means by which the article is "fixed" in the hollow channel provides for removal of the article from the hollow channel after a fluid (e.g., a disinfectant) has contacted the article.

In the illustrated device 200 of FIGS. 3 and 4, the body 30 comprises two parts (30*a* and 30*b*, respectively) that are joined together by complementary parts, such as threaded coupling parts, to form the body 30. It is contemplated that other joining means (e.g., an adhesive, a clamp, friction fit), can be used to join the parts of the body together to form the process challenge device. When assembled, the two parts of the body 30 form a first compartment (not shown) in the hollow channel 32 of the body 30. The first compartment is dimensioned to receive and retain the article 100 in the body 30. Optionally, the device 200 comprises a porous base 35 to support and/or confine the article 100 in the hollow channel 32. The porous base 35 is configured to permit the flow of liquid through the hollow channel 32 of the device

200. Optionally, the device 200 further comprises an O-ring 37 to secure the article 100 in the first compartment of the hollow channel.

The body 30 may be formed of a variety of suitable materials including, but not limited to, polymeric material (e.g., a thermoplastic polymer), metal, glass, or combinations thereof, using processes (e.g., injection molding) that are known in the art. Devices made using transparent and/or translucent materials (e.g., glass, plastic) can provide for in situ inspection of the article 100 during the disinfection process and/or while the article is analyzed after it was exposed to a disinfection process.

The article 100 is fixed in the hollow channel 32. In any embodiment, the article 100 can be removably fixed in the hollow channel 32. The article can be fixed in the hollow channel 32 using a variety of means including the use of an adhesive (e.g., a pressure-sensitive or hot-melt adhesive, not shown); the use of a clamp (not shown); and/or by dimensioning the article 100, the hollow channel 32, and first compartment 38 so that the article fits into the first compartment but is too large to pass through the hollow channel and out of the body 30; for example. The article 100 may be removed from the hollow channel 32, for example, by separating the two parts (30*a* and 30*b*, respectively) of the body 30 by unscrewing them to separate the two parts, thereby providing access to the article in the first compartment 38, and removing the article using forceps.

Advantageously, fixing the article 100 in the hollow channel 32 prevents the article, and the test microorganisms adhered thereto, from migrating out of the device 200 when a liquid (e.g. a liquid disinfectant is flowed through the hollow channel Advantageously, removably fixing the article 100 in the hollow channel 32 permits removal of the article by an operator in order to analyze the article for a presence of a viable test microorganisms (e.g., spore) adhered thereto.

In any embodiment, a process challenge device of the present disclosure may include optional features that facilitate coupling the device to a liquid flow system. For example, the device 200 of the illustrated embodiment of FIG. 2 comprises a Luer-type connector 40 (e.g., a female-type Luer connector or a male-type Luer connector) at the first aperture 31 of the hollow channel 32. The device 200 further can comprise an optional Luer-type connector (e.g., a female-type Luer connector or a male-type Luer connector, not shown) at the second aperture 33 of the hollow channel 32. In any embodiment, the Luer-type connector(s) can be Luer-slip connectors, Luer-lock connectors, or a combination of a Luer-slip connector and a Luer-lock connector. These connectors and/or other connectors known in the art can be used to attach the device 200 (e.g., via a tube, not shown) to a liquid flow system (e.g., in an automatic endoscope reprocessor (AER), not shown).

Figure 5:
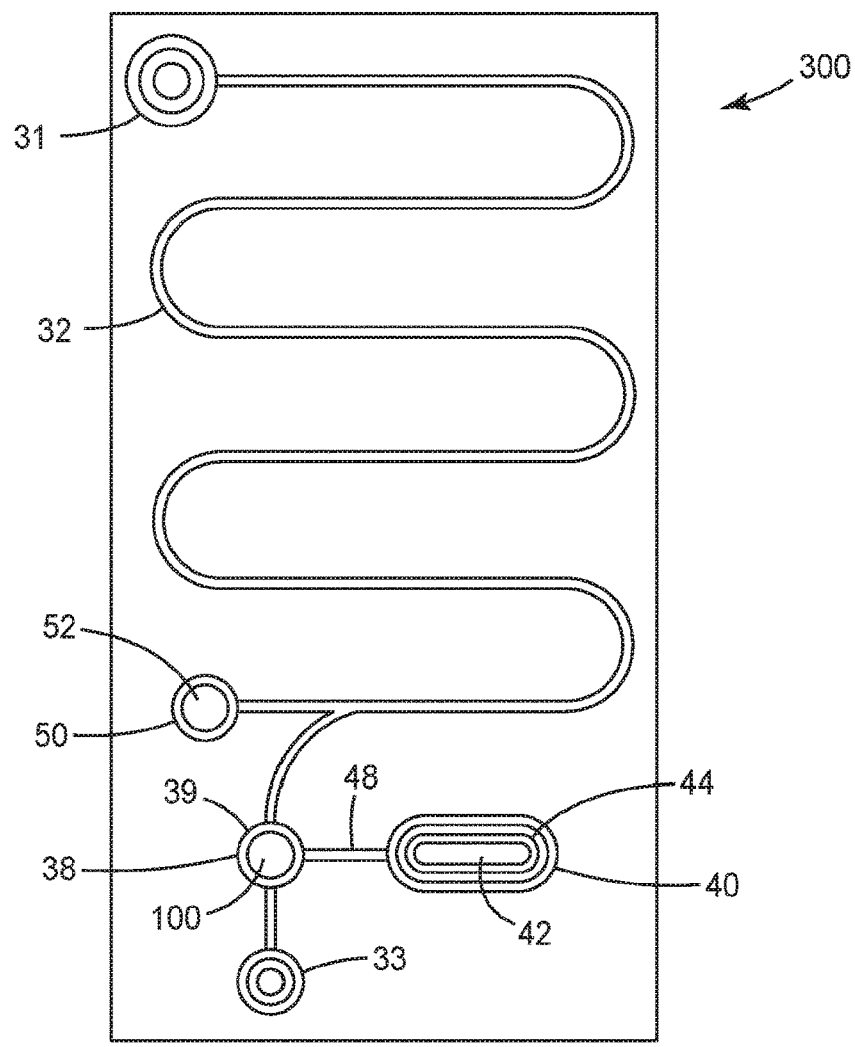
FIG. 5 shows a plan view of an alternative embodiment of a process challenge device according to the present disclosure.

FIG. 5 shows another embodiment of a process challenge device 300 according to the present disclosure. The device 300 is substantially planar and may be dimensioned to fit into an AER. A similar planar process challenge device is described in International Publication No. WO 2016/164329 A1, which is incorporated herein by reference in its entirety. The process challenge device 300 comprises a body 30 with a hollow channel 32 extending through the body from a first aperture 31 to a second aperture 33 that is spaced apart from the first aperture. The hollow channel 32 includes a first compartment 38 in which an article 100 is fixedly disposed. The article 100 can be any embodiment of the article comprising a substrate and a dried coating comprising a polymeric binding agent and a plurality of test microorganisms according to the present disclosure. The article 100 can be fixed in the hollow channel 32 according to any of the embodiments described herein.

In any embodiment, the first compartment 38 can comprise a wall 39 that permits optical evaluation of the contents (e.g., the article 100 and/or a detection medium or indicator compound as described herein) of the compartment. The wall 39 can be substantially transmissible to visible wavelengths of electromagnetic radiation and, optionally, may be substantially transmissible to ultraviolet and/or infrared wavelengths of electromagnetic radiation. Thus, for example, a color change in the contents of the first compartment 38 due to metabolic activity of the test microorganisms (e.g., spores) may be detected in the first compartment either visually or by using an optical detection instrument (e.g., a spectrophotometer or luminometer). Optionally, a portion of a wall forming the hollow channel 32 away from the first compartment may be optically transparent or translucent similarly, thereby permitting optical evaluation of the detection medium or indicator compound in the hollow channel at a location spaced apart from the first compartment.

The hollow channel 32 has a first aperture 31 and a second aperture 33 spaced apart from the first aperture. During use, a disinfectant (e.g., a liquid disinfectant) passing through the hollow channel from the first aperture to the second aperture contacts (e.g., passes around and/or through) the article 100 disposed in the hollow channel 32. The first aperture 31 and second aperture 33 can function as connection ports to attach the device 300 to a liquid flow system such as an automatic endoscope reprocessor (AER, not shown). For example, the first aperture 31 can be connected to an AER (e.g., via a suitable adapter or tube) to direct a portion of the liquid flow from the AER into the device 300 and the second aperture 33 can be connected to the AER (e.g., via a suitable adapter, such as the adapter described in U.S. Patent Application No. 62/407,749, filed on Oct. 13, 2016 and entitled "MICROBIAL INDICATOR DEVICE FOR USE WITH PROCESS MONITORING SYSTEMS", which is incorporated herein by reference in its entirety) to direct the portion back into the AER.

In any embodiment, the hollow channel 32 forms a tortuous (e.g., non-linear) liquid flow path. In the illustrated embodiment of FIG. 5, the liquid flow path formed by the hollow channel 32 comprises a plurality of arcuate bends that can simulate the bends in a luminal medical device such as a flexible endoscope, for example.

Optionally, the device 300 further comprises a reservoir 40 containing a detection medium 42. In any embodiment, the detection medium 42 is disposed in selective fluid communication with the article 100. Selective fluid communication can be imposed by the use of a valve (not shown), for example. Alternatively, as shown in the illustrated embodiment of FIG. 5, the detection medium 42 is contained in a frangible container 44 that is disposed in the reservoir 40 that is in fluid communication (e.g., via conduit 48) with the hollow channel 32. The frangible container 44 may be fabricated from glass, a metal film (e.g., a blister-pack), or plastic, for example. The valve, if present, may comprise a plastic film that bursts when external pressure (e.g., manual pressure) is applied to the second compartment, thereby permitting flow of the detection medium from the second compartment.

In use, the detection medium 42 passes from the reservoir 40 through the hollow channel 32 to the article 100. The detection medium 42 can be urged through the hollow channel 32 to the article 100 by a variety of forces including, for example, by positive pressure applied to the body 30 at the reservoir 40, by capillary action, by venturi force generated by flowing a liquid and/or gas through the hollow channel, or by applying negative pressure (e.g., from a vacuum source) to an aperture (e.g., the second aperture 33 shown in FIG. 5), wherein the first compartment 38 is disposed in the hollow channel 32 between the reservoir and the aperture.

The detection medium 42 comprises one or more reagent. In any embodiment, the reagent can be dissolved or suspended in an aqueous medium (e.g., water, an aqueous buffer). In any embodiment, the reagent may be an effective amount of a nutrient that facilitates germination and/or growth of the test microorganism (e.g. spores). Non-limiting examples of suitable nutrients include serine, proline, arginine, glutamate, asparagine, aspartate, threonine, lipids, fatty acids, potato infusion, yeast extract, malt extract, peptones, dextrose, and a combination of any two or more of the foregoing nutrients. Alternatively, or additionally, the reagent may be an indicator compound facilitates detection of a metabolic activity of the test microorganism (e.g., spore). In any embodiment, the metabolic activity can be an enzyme activity. Non-limiting examples of indicator compounds include a chromogenic enzyme substrate, a fluorogenic enzyme substrate, a pH indicator, a redox indicator, a chemiluminescent enzyme substrate, a dye, and a combination of any two or more of the foregoing indicator compounds. Alternatively, or additionally, the reagent may be an effective amount of a neutralizer compound that inhibits an antimicrobial activity of a disinfectant. Non-limiting examples of suitable neutralizer compounds include glycine, lecithin, sodium carbonate, potassium bicarbonate, ascorbic acid, sodium metabisulfite, horse serum, polyoxyethylene (20) sorbitan monooleate, catalase, sodium bisulfite, sodium bisulphate, sodium thioglycolate, and sodium thiosulfate. In some embodiments, the reagent can be a combination of any two or more reagents selected from the group consisting of a nutrient that facilitates germination and/or growth of the spores, an indicator compound facilitates detection of a metabolic activity of the test microorganism (spores), and an effective amount of a neutralizer compound that inhibits an antimicrobial activity of a disinfectant. In some embodiments, the neutralizer compound can be supplemented with an additive selected from the group consisting of lecithin, cysteine, histidine, and Tween 80.

Optionally, the device 300 can comprise a second compartment 50 that is in selective fluid communication (e.g., via a valve, not shown) with the hollow channel 32. The second compartment 50 may comprise the effective amount of the neutralizer compound 52 described herein. In any embodiment, the neutralizer compound 52 may be disposed in a frangible container (not shown) as described for the detection medium. In use, after the disinfectant flows through the hollow channel 32 and the article 100 is contacted with the disinfectant for at least a minimum contact time (as discussed hereinbelow), the neutralizer compound may be released from the second compartment to inactivate any residual disinfectant in the device.

In any embodiment, the device further comprises a chemical indicator (not shown) disposed in fluid communication with the hollow channel. The chemical indicator provides an indication that a particular disinfectant has passed through the hollow channel and contacted the chemical indicator thereby. Suitable chemical indicators include those described in U.S. Provisional Patent Application No. 62/332,243; filed on May 5, 2016, and entitled "METHOD OF DISINFECTING A MEDICAL DEVICE"; which is incorporated herein by reference in its entirety. The chemical indicator may be retained in the hollow channel (not shown) or in a third compartment (not shown) that is disposed in fluid communication with the hollow channel.

Figure 6:
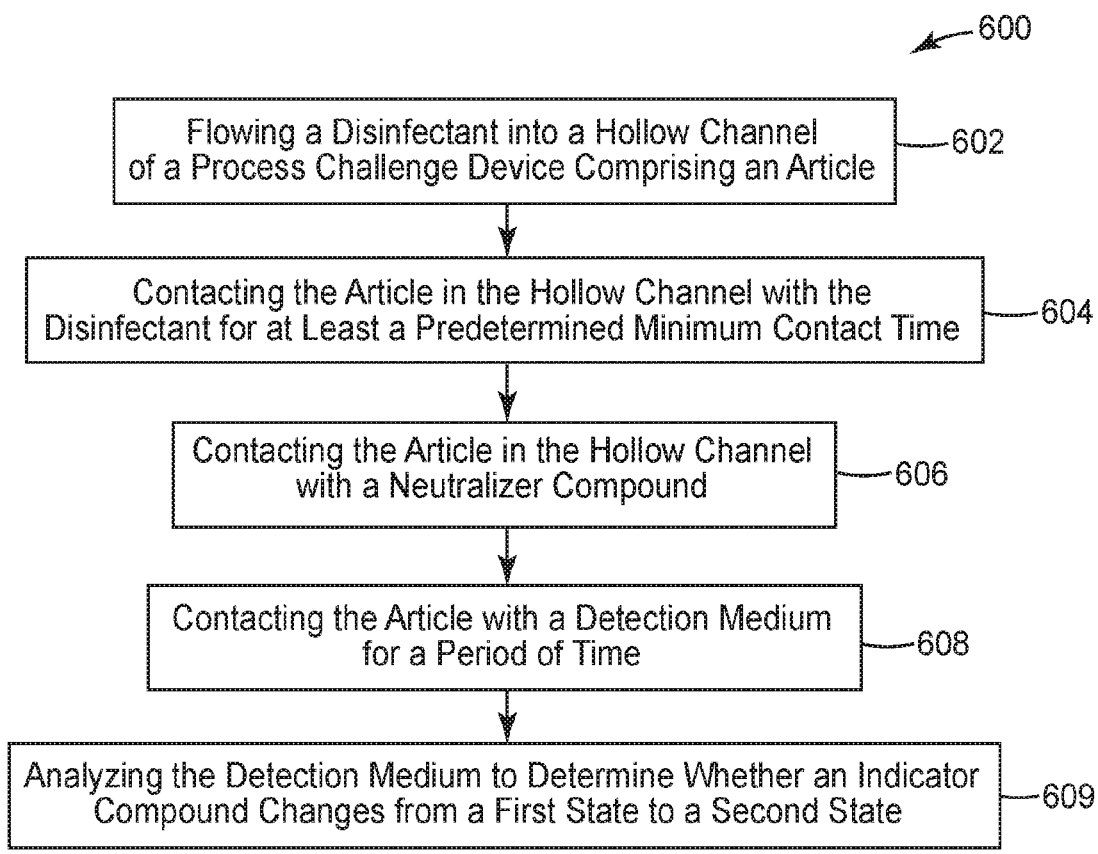
FIG. 6 shows a block diagram of one embodiment of a method according to the present disclosure.

In another aspect, the present disclosure provides a first method. The first method can be used to verify the efficacy of a disinfection process (e.g., a disinfection process using a liquid disinfectant). FIG. 6 shows a block diagram of one embodiment of the first method 600 according to the present disclosure. The first method 600 comprises a step 602 of flowing a disinfectant through the hollow channel of any embodiment of the process challenge device according to the present disclosure wherein the process challenge device comprises a reservoir containing the detection medium, wherein the detection medium comprises the effective amount of the nutrient and the indicator compound, wherein the device comprises a wall that forms the hollow channel, and wherein a portion of a wall permits optical evaluation of the spores or a product of metabolic activity of the spores. Flowing the disinfectant through the hollow channel comprises contacting the article with the disinfectant. In any embodiment, flowing the disinfectant through the hollow channel comprises flowing a disinfectant selected from a group consisting of ortho-phthalaldehyde, glutaraldehyde, peracetic acid, and hydrogen peroxide.

While flowing the disinfectant through the hollow channel and/or after flowing the disinfectant through the hollow channel, the first method 600 comprises the step 604 of contacting the article with the disinfectant in the hollow channel at a predefined temperature for at least a predetermined minimum contact time. Disinfection processes require contact between the disinfectant and the materials (e.g., articles) to be disinfected for a minimum period of contact at a predefined temperature in order to facilitate inactivation of microorganisms that are present on and/or in the materials to be disinfected. A person having ordinary skill in the art will recognize the minimum contact time may depend upon the composition of the disinfectant and/or the temperature at which the contact occurs. In general, contact between the materials and the disinfectant at higher temperatures requires less contact time to achieve inactivation of microorganisms than at lower temperatures.

Predefined temperatures for contacting disinfectants with materials to be disinfected are temperatures that are intentionally used in disinfection processes to facilitate inactivation of microorganisms. Typically, the predefined temperature is maintained (e.g., using an appropriate temperature-controlling apparatus) at a generally constant temperature throughout the process. Suitable predefined temperatures for processes that employ liquid disinfectants are within the range of about 20 degrees C. to about 60 degrees C. The minimum contact time can be from about 3 minutes to about 90 minutes, for example.

After contacting the article with the disinfectant in the hollow channel at the predefined temperature for at least the predetermined minimum contact time, the first method 600 comprises a step 606 of contacting the article with an effective amount of a neutralizer compound that inhibits an antimicrobial activity of the disinfectant. Inactivating ("neutralizing") the disinfectant used in the disinfection process prevents the disinfectant from continuing to inactivate the test microorganism after the completion of the disinfection process. Residual disinfectant that remains on or in the article after the minimum contact time of the process can be inactivated by contacting the article in the hollow channel with an appropriate chemical compound that is known in the art for neutralizing the particular disinfectant used in the first method 600. Suitable neutralizer compounds (for inactivating the disinfectant) include, for example, lethicin, glycine, sodium carbonate, potassium bicarbonate, ascorbic acid, sodium metabisulfite, horse serum, polyoxyethylene (20) sorbitan monooleate, catalase, sodium bisulfite, sodium bisulphate, sodium thioglycolate, sodium thiosulfate, or an enzyme (e.g., catalase).

The neutralizer compound can be provided to the article by several means. In some embodiments, the neutralizer is contained in a second reservoir in the process challenge device. The second reservoir, like the first reservoir described herein, is disposed in selective fluid communication with the article. Thus, after the article is contacted with the disinfectant for at least the minimum contact time, the effective amount of the neutralizer compound is released from the second reservoir (e.g., as described herein for the contents of the first reservoir) and contacted with the contents (e.g., the article) in the hollow channel, where the neutralizing compound inactivates residual disinfectant in the hollow channel and/or the article. In these embodiments, the neutralizer compound can be permitted to react with residual disinfectant in the hollow channel and/or the article for a period of time sufficient to inactivate the disinfectant. Subsequently, the detection medium can be contacted with the article in order to detect any surviving test microorganisms.

In some embodiments, the effective amount of neutralizer compound is provided in the detection medium and, thus, when the detection medium contacts the article, the effective amount neutralizer compound also contact the article and inactivates the disinfectant.

After contacting the article with an effective amount of the neutralizer compound, the first method 600 comprises the step 608 of contacting the article with the detection medium in the hollow channel for a period of time. The detection medium can comprise any embodiment of the detection medium disclosed herein. Contacting the article with the detection medium provides the operator with a means of detecting whether any of the plurality of test microorganisms (e.g., spores) were not inactivated by contact with the disinfectant. Detection of test microorganisms that were not inactivated by contact with the disinfectant can be performed using any of a variety of microorganism detection techniques that are known in the art including, for example, detection of spore germination, detection of microorganism growth, detection of microorganism reproduction, detection of a microorganism metabolic activity (e.g., an enzyme activity, fermentation of a nutrient, an oxidation/reduction reaction), and a combination of any two or more of the foregoing detection techniques. In any embodiment, contacting the article with the detection medium in the hollow channel for a period of time can comprise contacting the article with the detection medium at a temperature that facilitates a metabolic activity of the test microorganisms (e.g., the device can be incubated at a temperature suitable for growth and/or enzyme activity of the test microorganism).

Thus, after contacting the article with the detection medium in the hollow channel for the period of time, the first method 600 comprises the step 609 of analyzing the detection medium in the hollow channel to determine whether the indicator compound changed from a first state to a second state. The detection medium can be analyzed in situ (i.e., it can be analyzed while it is disposed in the hollow channel) or at least a portion of the detection medium can be removed from the hollow channel (e.g., through the first aperture of second aperture) and analyzed outside of the hollow channel.

Analyzing the detection medium can comprise visually observing the detection medium for a visible change from a first state to a second state. Alternatively or additionally, analyzing the detection medium can comprise placing the detection medium (e.g., in the process challenge device) into an instrument to analyze the detection medium for a change from a first state to a second state. In any embodiment, analyzing the detection medium can comprise comparing the detection medium of the process challenge device that was subjected to a disinfection process to a standard (e.g., a color comparison chart) and/or comparing the detection medium of the process challenge device that was subjected to a disinfection process to "control" (e.g., a second process challenge device that was not subjected to a disinfection process).

If at least one test microorganism survives contact with the disinfectant, metabolic activity of the surviving test microorganism will change the detection medium from a first state to a second state. For example, the detection medium may change from a substantially clear first state to a cloudy (turbid) or substantially opaque second state. The appearance of turbidity in the detection medium may be evidence of germination and/or growth of the test microorganism after contact with the disinfectant, indicating survival of at least one of the plurality of test microorganisms and possibly indicating the disinfection process was not efficacious. Alternatively, or additionally, the detection medium may change from a first colored state to a second colored state (e.g., due to conversion of a pH indicator, a redox indicator, or an enzyme substrate resulting from metabolic activity of a test microorganism that survived the disinfection process). In some embodiments, the first colored state can be relatively less colored (or colorless) and the second colored state can be more colored. In some embodiments, the first colored state can be relatively more colored and the second colored state can be relatively less colored (or colorless). In some embodiments, the first colored state can have a first color and the second colored state can have a second color that is different than the first color.

Figure 7:
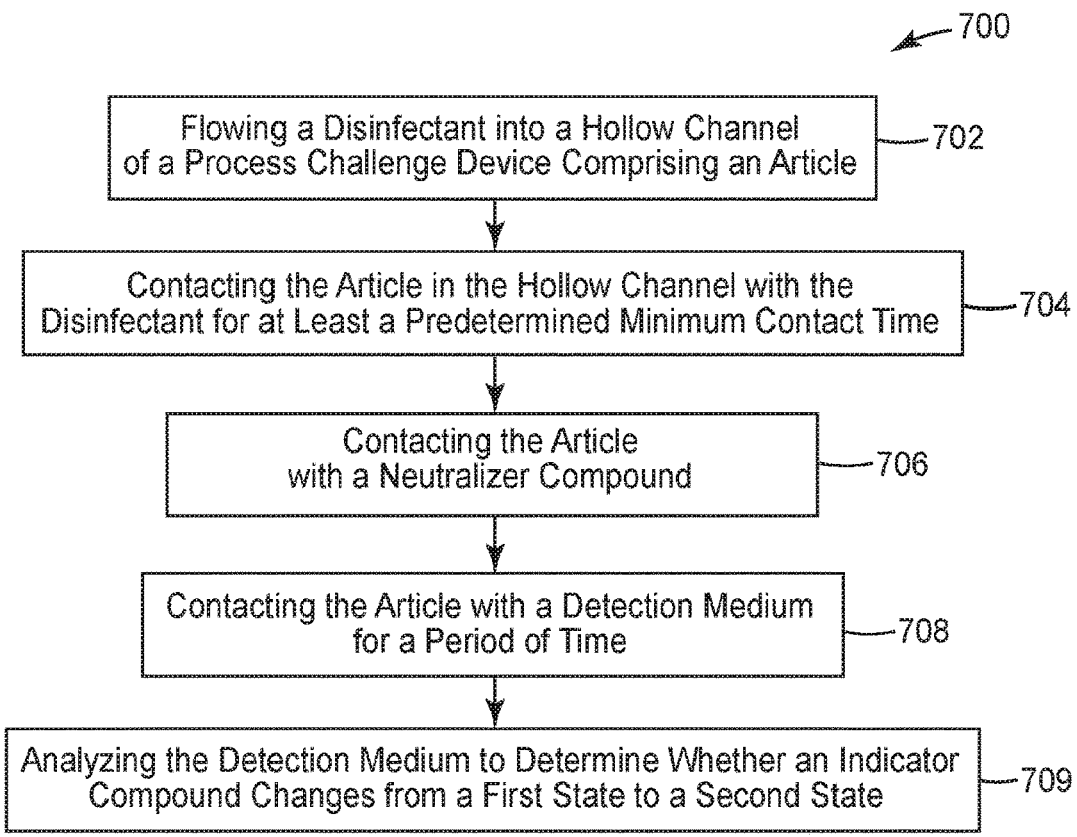
FIG. 7 shows a block diagram of one embodiment of another method according to the present disclosure.

In another aspect the present disclosure provides a second method. The second method can be used to verify the efficacy of a disinfection process (e.g., a disinfection process using a liquid disinfectant). FIG. 7 shows a block diagram of one embodiment of the second method 700 according to the present disclosure. The second method 700 comprises a step 702 of flowing a disinfectant through the hollow channel of any embodiment of the process challenge device according to the present disclosure. Flowing the disinfectant through the hollow channel comprises contacting the article with the disinfectant. In any embodiment, flowing the disinfectant through the hollow channel comprises flowing a disinfectant selected from a group consisting of ortho-phthalaldehyde, glutaraldehyde, peracetic acid, and hydrogen peroxide.

While flowing the disinfectant through the hollow channel and/or after flowing the disinfectant through the hollow channel, the second method 700 comprises the step 704 of contacting the article with the disinfectant in the hollow channel at a predefined temperature for at least a predetermined minimum contact time. Disinfection processes require contact between the disinfectant and the materials (e.g., articles) to be disinfected for a minimum period of contact at a predefined temperature in order to facilitate inactivation of microorganisms that are present on and/or in the materials to be disinfected. A person having ordinary skill in the art will recognize the minimum contact time may depend upon the composition of the disinfectant and/or the temperature at which the contact occurs. In general, contact between the materials and the disinfectant at higher temperatures requires less contact time to achieve inactivation of microorganisms than at lower temperatures.

Predefined temperatures for contacting disinfectants with materials to be disinfected are temperatures that are intentionally used in disinfection processes to facilitate inactivation of microorganisms. Typically, the predefined temperature is maintained (e.g., using an appropriate temperature-controlling apparatus) at a generally constant temperature throughout the process. Suitable predefined temperatures for processes that employ liquid disinfectants are within the range of about 20 degrees C. to about 60 degrees C.

After contacting the article with the disinfectant in the hollow channel at the predefined temperature for at least the minimum contact time, the second method 700 comprises the step 706 of contacting the article with an effective amount of a neutralizer compound that inhibits an antimicrobial activity of the disinfectant. Inactivating ("neutralizing") the disinfectant used in the disinfection process prevents the disinfectant from continuing to inactivate the test microorganism after the completion of the disinfection process. Residual disinfectant that remains on or in the article after the minimum contact time of the process can be inactivated by contacting the article with an appropriate chemical compound that is known in the art for neutralizing the particular disinfectant used in the second method 700. Suitable neutralizer compounds (for inactivating the disinfectant) include, for example, lethicin, glycine, sodium carbonate, potassium bicarbonate, ascorbic acid, sodium metabisulfite, horse serum, polyoxyethylene (20) sorbitan monooleate, catalase, sodium bisulfate, sodium bisulphate, sodium thioglycolate, sodium thiosulfate and an enzyme (e.g., catalase).

The neutralizer compound can be provided to the article by several means. For example, the neutralizer compound can be flowed into a hollow channel in which the article is disposed or the neutralizer compound can be added (e.g. by pipet) into a reaction tube in which the article is disposed. In these embodiments, the neutralizer compound can be permitted to react with residual disinfectant in the hollow channel and/or the article for a period of time sufficient to inactivate the disinfectant. Subsequently, the detection medium can be contacted with the article in order to detect any surviving test microorganisms.

In some embodiments of the second method 700, the effective amount of neutralizer compound is provided in the detection medium and, thus, when the detection medium contacts the article, the effective amount neutralizer compound also contact the article and inactivates the disinfectant.

After contacting the article with the neutralizer compound, the method 700 comprises a step 708 of contacting the article with the detection medium. The detection medium can comprise any embodiment of the detection medium disclosed herein. Contacting the article with the detection medium provides the operator with a means of detecting whether any of the plurality of test microorganisms (e.g., spores) were not inactivated by contact with the disinfectant. Detection of test microorganisms that were not inactivated by contact with the disinfectant can be performed using any of a variety of microorganism detection techniques that are known in the art including, for example, detection of spore germination, detection of microorganism growth, detection of microorganism reproduction, detection of a microorganism metabolic activity (e.g., an enzyme activity, fermentation of a nutrient, an oxidation/reduction reaction), and a combination of any two or more of the foregoing detection techniques. In any embodiment, contacting the article with the detection medium in a hollow channel of a process challenge device, as described herein. In any embodiment, contacting the article with the detection medium for a period of time can comprise contacting the article with the detection medium at a temperature that facilitates a metabolic activity of the test microorganisms (e.g., the device can be incubated at a temperature suitable for growth and/or enzyme activity of the test microorganism).

Thus, after contacting the article with the detection medium for the period of time, the second method 700 comprises the step 709 of analyzing the detection medium to determine whether the indicator compound changed from a first state to a second state. The detection medium can be analyzed in situ (i.e., it can be analyzed while it is disposed in the hollow channel) or at least a portion of the detection medium can be removed from the hollow channel (e.g., through the first aperture of second aperture) and analyzed outside of the hollow channel Analyzing the detection medium can be performed according to any of the analyzing techniques or approaches described herein.

If at least one test microorganism survives contact with the disinfectant, metabolic activity of the surviving test microorganism will change the detection medium from a first state to a second state. The change from the first state to the second state can be any of the possible changes described hereinabove. A change in the detection medium from a first state to a second state that occurs due to metabolic activity of a surviving test microorganism can be an indication that the disinfection process was not efficacious.

In any embodiment of the second method, before contacting the article with the detection medium for a period of time, the second method further may comprise a step of removing the article from the process challenge device (not shown in FIG. 7). The article can be removed, for example, by using a process challenge device adapted to be opened in order to provide access to the article. In these embodiments, the process challenge device can be opened and sterile forceps can be used to remove the article.

Figure 8:
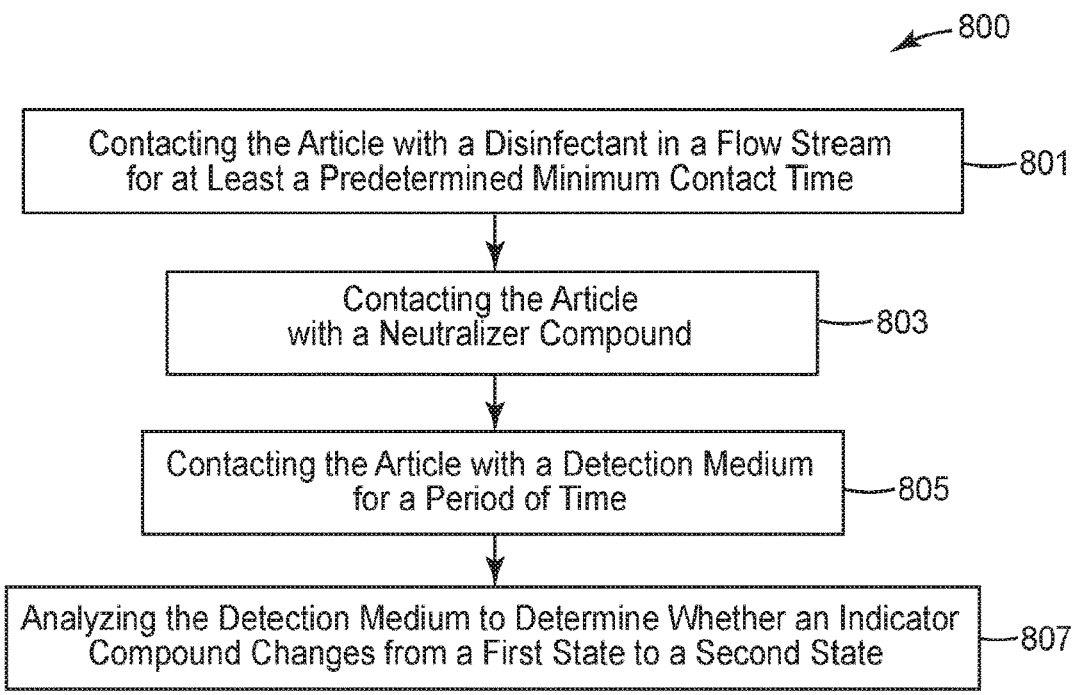
FIG. 8 shows a block diagram of one embodiment of yet another method according to the present disclosure.

In another aspect, the present disclosure provides a third method. The third method can be used to verify the efficacy of a disinfection process (e.g., a disinfection process using a liquid disinfectant). FIG. 8 shows a block diagram of one embodiment of the third method 800 according to the present disclosure. The third method 800 comprises a step 801 of contacting any embodiment of the article according to the present disclosure with a disinfectant in a flow stream for at least a predefined minimum contact time. In any embodiment, immersing the article in the disinfectant comprises immersing the article in a disinfectant selected from a group consisting of ortho-phthalaldehyde, glutaraldehyde, peracetic acid, and hydrogen peroxide. The flow stream may be a flow stream of disinfectant in an AER, for example. The article may be held at a particular location in the flow stream using any suitable holding means (e.g., a clamp, a harness, a clip, a hanger, a manifold).

Contacting the article with the disinfectant comprises contacting the article with the disinfectant at a predefined temperature for at least a predetermined minimum contact time. Disinfection processes require contact between the disinfectant and the materials (e.g., articles) to be disinfected for a minimum period of contact at a predefined temperature in order to facilitate inactivation of microorganisms that are present on and/or in the materials to be disinfected. A person having ordinary skill in the art will recognize the minimum contact time may depend upon the composition of the disinfectant and/or the temperature at which the contact occurs. In general, contact between the materials and the disinfectant at higher temperatures requires less contact time to achieve inactivation of microorganisms than at lower temperatures.

Predefined temperatures for contacting disinfectants with materials to be disinfected are temperatures that are intentionally used in disinfection processes to facilitate inactivation of microorganisms. Typically, the predefined temperature is maintained (e.g., using an appropriate temperature-controlling apparatus) at a generally constant temperature throughout the process. Suitable predefined temperatures for processes that employ liquid disinfectants are within the range of about 20 degrees C. to about 60 degrees C.

After contacting the article with the disinfectant at the predefined temperature for at least the minimum contact time, the third method 800 comprises the step 803 of contacting the article with an effective amount of a neutralizer compound that inhibits an antimicrobial activity of the disinfectant. Inactivating ("neutralizing") the disinfectant used in the disinfection process prevents the disinfectant from continuing to inactivate the test microorganism after the completion of the disinfection process. Residual disinfectant that remains on or in the article after the minimum contact time of the process can be inactivated by contacting the article with an appropriate chemical compound that is known in the art for neutralizing the particular disinfectant used in the third method 800. Suitable neutralizer compounds (for inactivating the disinfectant) include, for example, lethicin, glycine, sodium carbonate, potassium bicarbonate, ascorbic acid, sodium metabisulfite, horse serum, polyoxyethylene (20) sorbitan monooleate, catalase, sodium bisulfite, sodium bisulphate, sodium thioglycolate, sodium thiosulfate and an enzyme (e.g., catalase).

The neutralizer compound can be provided to the article by several means. For example, the neutralizer compound can be flowed into a hollow channel in which the article is disposed or the neutralizer compound can be added (e.g. by pipet) into a reaction tube in which the article is disposed. In these embodiments, the neutralizer compound can be permitted to react with residual disinfectant in the hollow channel and/or the article for a period of time sufficient to inactivate the disinfectant. Subsequently, the detection medium can be contacted with the article in order to detect any surviving test microorganisms.

In some embodiments of the third method 800, the effective amount of neutralizer compound is provided in the detection medium and, thus, when the detection medium contacts the article, the effective amount neutralizer compound also contact the article and inactivates the disinfectant.

In any of the above embodiments of the method, as an alternative to contacting the article with an effective amount of a neutralizer compound, the method can comprise a step of rinsing the article with a rinse solvent in order to reduce the quantity (and/or concentration) of disinfectant proximate the test microorganisms. For example, after flowing a disinfectant through a hollow channel that houses an article of the present disclosure, the article may retain an effective amount of the disinfectant even after the flow is discontinued. The retained effective amount of disinfectant may continue to inactivate (e.g., render nonviable) the test microorganisms until the effective amount is either inactivated by a neutralizer compound as described herein and/or until the disinfectant is diluted (e.g., by rinsing) to a concentration that is no longer effective to inactivate the test microorganism.

Similarly, after contacting an article of the present disclosure with a disinfectant (e.g., by dipping the article into a disinfectant solution), the article may retain an effective amount of the disinfectant even after the article is removed from the disinfectant. The retained effective amount of disinfectant may continue to inactivate (e.g., render nonviable) the test microorganisms until the effective amount is either inactivated by a neutralizer compound as described herein and/or until the disinfectant is diluted (e.g., by rinsing) to a concentration that is no longer effective to inactivate the test microorganism.

In some embodiments (i.e., wherein the article is disposed in the hollow channel of a device as disclosed herein), the article is rinsed by flowing a rinse solvent through the hollow channel and thereby reducing (e.g., by dilution) the amount (and/or concentration) of disinfectant present in the hollow channel, in general, and the amount of disinfectant in the article, in particular.

In some embodiments, the article is contacted with the rinse solvent by dipping or placing the article into a container holding the rinse solvent. The article is allowed to contact the rinse solvent for a period of time sufficient to reduce the quantity (and/or concentration) of disinfectant proximate the test microorganisms.

The rinse solvent can be any solvent capable of contacting an article of the present disclosure, wherein the article is optionally disposed in a hollow channel of a device, without substantially decreasing the number of viable test microorganisms disposed in the coating on the article. In any embodiment, the rinse solvent may comprise an aqueous liquid. Optionally, the rinse solvent may comprise solutes (e.g., inorganic salts, organic or inorganic buffer reagents, carbohydrates) for maintaining a suitable osmolarity and/or pH to support viability of the test microorganism. Optionally, the rinse solvent may comprise a surface-active agent (e.g., TWEEN 80 surfactant solution) that does not substantially decrease the viability of the test microorganism. In any embodiment, the rinse solvent may comprise a liquid in which the disinfectant is soluble. Preferably, the rinse solvent is substantially free of viable bacteria, filamentous fungi, or spores thereof. More preferably, the rinse solvent is sterile.

Non-limiting examples of suitable rinse solvents include water, phosphate-buffered saline, and an aqueous solution comprising 0.05% TWEEN 80 surfactant.

After contacting the article with the neutralizer compound, the third method 800 comprises a step 805 of contacting the article with the detection medium. The detection medium can comprise any embodiment of the detection medium disclosed herein. The article can be contacted with the detection medium in any suitable container (e.g., a sterile reaction tube). The article can be transferred into the detection medium using sterile forceps, for example. Contacting the article with the detection medium provides the operator with a means of detecting whether any of the plurality of test microorganisms (e.g., spores) were not inactivated by contact with the disinfectant. Detection of test microorganisms that were not inactivated by contact with the disinfectant can be performed using any of a variety of microorganism detection techniques that are known in the art including, for example, detection of spore germination, detection of microorganism growth, detection of microorganism reproduction, detection of a microorganism metabolic activity (e.g., an enzyme activity, fermentation of a nutrient, an oxidation/ reduction reaction), and a combination of any two or more of the foregoing detection techniques. In any embodiment, contacting the article with the detection medium can comprise contacting the article with the detection medium at a temperature that facilitates a metabolic activity of the test microorganisms (e.g., the device can be incubated at a temperature suitable for growth and/or enzyme activity of the test microorganism).

Thus, after contacting the article with the detection medium for the period of time, the third method 800 comprises the step 807 of analyzing the detection medium to determine whether the indicator compound changed from a first state to a second state. The detection medium can be analyzed in situ (i.e., it can be analyzed while it is disposed in the container in which it is contacted with the article) or at least a portion of the detection medium can be removed from the container and analyzed outside of the container. Analyzing the detection medium can be performed according to any of the analyzing techniques or approaches described herein.

If at least one test microorganism survives contact with the disinfectant, metabolic activity of the surviving test microorganism will change the detection medium from a first state to a second state. For example, the detection medium may change from a substantially clear first state to a cloudy (turbid) or substantially opaque second state. The appearance of turbidity in the detection medium may be evidence of germination and/or growth of the test microorganism after contact with the disinfectant, indicating survival of at least one of the plurality of test microorganisms and possibly indicating the disinfection process was not efficacious. Alternatively, or additionally, the detection medium may change from a first colored state to a second colored state (e.g., due to conversion of a pH indicator, a redox indicator, or an enzyme substrate resulting from metabolic activity of a test microorganism that survived the disinfection process). In some embodiments, the first colored state can be relatively less colored (or colorless) and the second colored state can be more colored. In some embodiments, the first colored state can be relatively more colored and the second colored state can be relatively less colored (or colorless). In some embodiments, the first colored state can have a first color and the second colored state can have a second color that is different than the first color.

In some embodiments, before contacting the article with the detection medium, the second method and the third method optionally comprise a step of contacting the article with an effective amount of a neutralizer compound that inhibits an antimicrobial activity of the disinfectant. The neutralizer compound can be flowed into the hollow channel of a process challenge device in which the article is disposed or the neutralizer compound can be deposited into a reaction tube containing the article, as described herein. Alternatively, or additionally, the neutralizer compound can be provided in the detection medium so that, when the detection medium contacts the article, the neutralizer compound also contacts the article.

In some embodiments, before contacting the article with the detection medium, the method can optionally comprise a step of contacting the article with an effective amount of a sterilant. Suitable sterilant includes, but are not limited to, a gas plasma, vaporized hydrogen peroxide, ozone, chlorine dioxide, peracetic acid, ethylene oxide or ions derived therefrom. Sterilization is generally defined as the process of completely destroying all viable sources of biological activity, such as microorganisms, including structures such as viruses and spores.

A person having ordinary skill in the art will recognize, in order to decontaminate or sterilize an object (e.g., the article of the present disclosure), the efficacy of the process depends on the quantity of sterilant (e.g., the concentration of sterilant), the length of time to which the object is exposed to the sterilant, and may depend upon other factors such as, for example, the temperature of the load, relative humidity, and the amount and/or type (e.g. absorbent property, relative to the sterilant) of material used in the sterilization. The Examples below provide general guidance for a typical process; however the parameters can be varied according to the desired result, as is well known by a person having ordinary skill in the art.

In any embodiment of any of the methods of the present disclosure, the minimum contact time can be about 3 minutes to about 90 minutes. In any embodiment of any of the methods of the present disclosure, contacting the article with the detection medium for a period of time comprises contacting the article with the detection medium for about 5 minutes to about 48 hours.

In any embodiment of any of the methods of the present disclosure wherein the test microorganisms comprise spores, analyzing the detection medium to detect a biological activity of the test microorganisms comprises detecting vegetative cells derived from germination and/or outgrowth of the spores.

In any embodiment of any of the methods of the present disclosure wherein the test microorganisms comprise spores, analyzing the detection medium to detect a biological activity of the test microorganisms comprises detecting an enzyme activity of the spores and/or an enzyme activity of vegetative cells derived from germination and/or outgrowth of the spores. In any embodiment, detecting an enzyme activity comprises detecting an enzyme activity selected from the list of consisting of phosphatase (e.g., acid phosphatase or alkaline phosphatase) activity, beta-glucosidase activity, alpha-glucosidase activity, cellulase activity, xylanase activity, beta-glucuronidase activity, alpha-glucuronidase activity, alpha-galactosidase activity, beta-galactosidase activity, laccase activity, protease activity, peptidase activity, amylase activity, glucose oxidase activity, lyase activity, esterase activity, lipase activity, oxidoreductase activity, and a combination of any two or more of the foregoing enzyme activities.

In any embodiment of any of the methods of the present disclosure, contacting the article with the detection medium for a period of time comprises contacting the article with the detection medium at a predefined temperature. The predefined temperature may vary according to the test microorganism. Suitable predefined temperatures may include temperatures in the range from about 20 degrees C. to about 65 degrees C., for example.

In any embodiment of any of the methods of the present disclosure, after contacting the article in the disinfectant for at least a predetermined period of time, less than 5% of the test microorganisms (e.g. spores) are washed off the article.

In any embodiment of any of the methods of the present disclosure, after contacting the article in the disinfectant for at least a predetermined period of time, less than 2.5% of the test microorganisms (e.g. spores) are washed off the article In any embodiment of any of the methods of the present disclosure, after contacting the article in the disinfectant for at least a predetermined period, less than 2% of the test microorganisms (e.g. spores) are washed off the article In a preferred embodiment of any of the methods of the present disclosure, after contacting the article in the disinfectant for at least a predetermined period of time, less than 1% of the test microorganisms (e.g. spores) are washed off the article.

In a more preferred embodiment of any of the methods of the present disclosure, after contacting the article in the disinfectant for at least a predetermined period of time, less than 0.5% of the test microorganisms (e.g. spores) are washed off the article.

The predetermined period of time for contacting the article with the disinfectant can be at least 1 minute, or at least 3 minutes, or at least 5 minutes, or at least 15 minutes, or at least 30 minutes, or in some cases at least 60 minutes.

EXEMPLARY EMBODIMENTS

Embodiment A is an article, comprising
a nonwoven substrate having a copolymer grafted thereto, the copolymer comprising interpolymerized monomer units of
a cationic nitrogen-containing ligand monomer selected from quaternary ammonium-containing and/or guanidinyl-containing ligand monomers;
an amide monomer;
an oxy monomer; and
a dried coating adhered to the substrate, the dried coating comprising a plurality of test microorganisms.

Embodiment B is the article of Embodiment A, wherein the grafted copolymer comprises:
a) 10 to 50 parts by weight of the cationic nitrogen-containing ligand monomer;
b) 10 to 80 parts by weight of the amide monomer;
c) 10 to 40 parts by weight of the oxy monomer; and
d) 0 to 30 parts by weight of a poly(alkylene oxide) monomer,
wherein the sum of a) to d) is 100 parts by weight.

Embodiment C is the article of Embodiment A or Embodiment B, wherein the dried coating further comprises a water-soluble or water-dispersible polymeric binding agent.

Embodiment D is the article of Embodiment C, wherein at least a portion of the plurality of test microorganisms is dispersed in the polymeric binding agent.

Embodiment E is the article of any one of the preceding Embodiments, wherein the nonwoven substrate comprises meltblown microfibers of a hydrophobic thermoplastic polyolefin.

Embodiment F is the article of any one of the preceding Embodiments, wherein the nonwoven substrate has a surface area of 15 to 50 $m^2$ per square meter of nonwoven substrate.

Embodiment G is the article of any one of the preceding Embodiments, wherein the nonwoven substrate has a solidity of less than 20%.

Embodiment H is the article of any one of the preceding Embodiments, the article has a weight ratio of copolymer to nonwoven substrate, wherein the weight ratio is about 0.5 to 3 parts copolymer to 1 part nonwoven substrate.

Embodiment I is the article of any one of the preceding Embodiments, wherein the water-soluble or water-dispersible polymeric binding agent is selected from the group consisting of agarose, polyvinylpyrrolidone, poly(alkylene oxide), and a combination of any two or more of the foregoing polymeric binding agents.

Embodiment J is the article of any one of the preceding Embodiments, wherein the plurality of test microorganisms comprises bacteria.

Embodiment K is the article of Embodiment J, wherein the bacteria comprise bacteria of a species of *Mycobacterium*.

Embodiment L is the article of any one of Embodiments A through J, wherein the plurality of test microorganisms comprises spores.

Embodiment M is the article of Embodiment L, wherein the spores comprise spores of a species of filamentous fungi.

Embodiment N is the article of Embodiment M, wherein the spores comprise spores of a species of *Aspergillus*.

Embodiment O is the article of Embodiment N, wherein the spores comprise spores of *Aspergillus brasiliensis, Aspergillus oryzae, Aspergillus niger*, or *Aspergillus nidulans*.

Embodiment P is the article of any one of the preceding Embodiments, wherein the plurality of viable test microorganisms consists of about 10 test microorganisms to about $10^8$ test microorganisms.

Embodiment Q is the article of any one of the preceding Embodiments, wherein the water-soluble or water-dispersible polymeric binding agent comprises poly(alkylene oxide), wherein the poly(alkylene oxide) has a weight average molecular weight of 400 Daltons, 4,000 Daltons, or 20,000 Daltons.

Embodiment R is the article of any one of the preceding Embodiments, wherein the quaternary ammonium-containing monomer used to make the copolymer comprises [3-(Methacryloylamino)propyl]trimethylammonium chloride.

Embodiment S is the article of any one of the preceding Embodiments, wherein the quaternary ammonium-containing monomer used to make the copolymer comprises [3-(Methacryloylamino)propyl]trimethylammonium chloride, the oxy monomer used to make the copolymer comprises glycidyl methacrylate, and the amide monomer used to make the copolymer comprises N-vinyl pyrrolidone.

Embodiment T is a process challenge device, comprising:
a body with a hollow channel having a first aperture and a second aperture spaced apart from the first aperture; and
the article of any one of the preceding claims fixedly disposed in the hollow channel.

Embodiment U is the process challenge device of Embodiment T, further comprising a reservoir containing a detection medium, wherein the reservoir is disposed in selective fluid communication with the article.

Embodiment V is the process challenge device of Embodiment U, wherein the detection medium comprises a reagent selected from the group consisting of a nutrient that facilitates germination and/or growth of the test microorganisms, an indicator compound facilitates detection of a test microorganism metabolic activity, an effective amount of a neutralizer compound that inhibits the antimicrobial activity of a disinfectant, and a combination of any two or more of the foregoing reagents.

Embodiment W is the process challenge device of Embodiment V, wherein the nutrient is selected from the group consisting of serine, proline, arginine, glutamate, asparagine, aspartate, threonine, lipids, fatty acids, potato infusion, yeast extract, malt extract, peptones, dextrose, and a combination of any two or more of the foregoing nutrients.

Embodiment X is the process challenge device of any one of Embodiments U through W, wherein the indicator compound is selected from the group consisting of a chromogenic enzyme substrate, a fluorogenic enzyme substrate, a pH indicator, a redox indicator, a chemiluminescent enzyme substrate, a dye, and a combination of any two or more of the foregoing indicator compounds.

Embodiment Y is the process challenge device of any one of Embodiments U through X, wherein the neutralizer compound is selected from the group consisting of glycine, sodium carbonate, potassium bicarbonate, ascorbic acid, sodium metabisulfite, horse serum, polyoxyethylene (20) sorbitan monooleate, catalase, sodium bisulfate, sodium bisulphate, sodium thioglycolate, and sodium thiosulfate.

Embodiment Z is the process challenge device of any one of Embodiments U through Y, wherein the article is disposed in the hollow channel such that a fluid passing through the hollow channel from the first aperture to the second aperture contacts the article Embodiment AA is the process challenge device of any one of Embodiments U through Z, wherein the body comprises a wall that forms the hollow channel, wherein a portion of a wall permits optical evaluation of the test microorganisms or a product of metabolic activity of the test microorganisms.

Embodiment AB is a method, comprising:

flowing an effective amount of a disinfectant through the hollow channel of the process challenge device of Embodiment AA, wherein the process challenge device comprises the reservoir containing the detection medium, wherein the detection medium comprises the effective amount of the nutrient and the indicator compound, wherein flowing the disinfectant through the hollow channel comprises contacting the article with the disinfectant;

while flowing the disinfectant through the hollow channel and/or after flowing the disinfectant through the hollow channel, contacting the article with the disinfectant in the hollow channel at a predefined temperature for at least a predetermined minimum contact time;

after contacting the article with the disinfectant in the hollow channel at the predefined temperature for at least the predetermined minimum contact time, contacting the article with an effective amount of a neutralizer compound that inhibits an antimicrobial activity of the disinfectant;

contacting the article with the detection medium in the hollow channel for a period of time; and after contacting the article with the detection medium in the hollow channel for the period of time, analyzing the detection medium in the hollow channel to determine whether the indicator compound changed from a first state to a second state.

Embodiment AC is the method of Embodiment AB, wherein flowing the disinfectant through the hollow channel of the process challenge device comprises flowing a disinfectant selected from the group consisting of ortho-phthalaldehyde, glutaraldehyde, peracetic acid, a disinfecting composition comprising peracetic acid and hydrogen peroxide, 12% (w/w) 2-propanol, a disinfecting composition comprising 2% (w/w) glutaraldehyde and 12% (w/w) 2-propanol, and hydrogen peroxide.

Embodiment AD is the method of Embodiment AB or Embodiment AC, wherein analyzing the detection medium in the hollow channel to determine whether the indicator compound changed from a first state to a second state comprises analyzing the indicator compound visually.

Embodiment AE is the method of Embodiment AB or Embodiment AC, wherein analyzing the detection medium in the hollow channel to determine whether the indicator compound changed from a first state to a second state comprises analyzing the indicator compound by using an automated detector.

Embodiment AF is the method of any one of Embodiments AB through AE, wherein the effective amount of the disinfectant is a quantity of the disinfectant that is sufficient to render all of the test microorganisms nonviable.

Embodiment AG is a method, comprising:

flowing an effective amount of a disinfectant through the hollow channel of the process challenge device of Embodiment AA, wherein the process challenge device comprises the reservoir containing the detection medium, wherein the detection medium comprises the effective amount of the nutrient and the indicator compound, wherein flowing the disinfectant through the hollow channel comprises contacting the article with the disinfectant;

while flowing the disinfectant through the hollow channel and/or after flowing the disinfectant through the hollow channel, contacting the article with the disinfectant in the hollow channel at a predefined temperature for at least a predetermined minimum contact time;

after contacting the article with the disinfectant in the hollow channel at the predefined temperature for at least the predetermined minimum contact time, flowing a rinse solvent through the hollow channel in order to displace a quantity of the disinfectant from the hollow channel;

contacting the article with the detection medium in the hollow channel for a period of time; and after contacting the article with the detection medium in the hollow channel for the period of time, analyzing the detection medium in the hollow channel to determine whether the indicator compound changed from a first state to a second state.

Embodiment AH is the method of Embodiment AG, wherein the effective amount of the disinfectant is a quantity of the disinfectant that is sufficient to render all of the test microorganisms nonviable.

Embodiment AI is method, comprising:

flowing an effective amount disinfectant through the hollow channel of the process challenge device of any one of Embodiments U through AA, wherein flowing the disinfectant through the hollow channel comprises contacting the article with the disinfectant;

while flowing the disinfectant through the hollow channel and/or after flowing the disinfectant through the hollow channel, contacting the article with the disinfectant in the hollow channel at a predefined temperature for at least a predetermined minimum contact time;

after contacting the article with the disinfectant for at least the minimum contact time, contacting the article with an effective amount of a neutralizer compound that inhibits an antimicrobial activity of the disinfectant;

contacting the article with the detection medium for a period of time; and after contacting the article with the detection medium for a period of time, analyzing the detection medium to detect a biological activity of the test microorganisms.

Embodiment AJ is the method of Embodiment AI wherein, after contacting the article with the disinfectant and before contacting the article with the detection medium, the method further comprises removing the article from the process challenge device.

Embodiment AK is the method of Embodiment AI or Embodiment AJ, wherein the effective amount of the disinfectant is a quantity of the disinfectant that is sufficient to render all of the test microorganisms nonviable.

Embodiment AL is a method, comprising:

flowing an effective amount disinfectant through the hollow channel of the process challenge device of any one of Embodiments U through AA, wherein flowing the disinfectant through the hollow channel comprises contacting the article with the disinfectant;

while flowing the disinfectant through the hollow channel and/or after flowing the disinfectant through the hollow channel, contacting the article with the disinfectant in the hollow channel at a predefined temperature for at least a predetermined minimum contact time;

after contacting the article with the disinfectant for at least the minimum contact time, flowing a rinse solvent through the hollow channel in order to displace a quantity of the disinfectant from the hollow channel;

contacting the article with the detection medium for a period of time; and after contacting the article with the detection medium for a period of time, analyzing the detection medium to detect a biological activity of the test microorganisms.

Embodiment AM is the method of Embodiment AL, wherein the effective amount of the disinfectant is a quantity of the disinfectant that is sufficient to render all of the test microorganisms nonviable.

Embodiment AN is a method, comprising:

contacting the article of any one of Embodiments T through AA with a disinfectant in a flow stream for at least a predefined minimum contact time;

after contacting the article with the disinfectant for the minimum contact time period, contacting the article with an effective amount of a neutralizer compound that inhibits an antimicrobial activity of the disinfectant;

contacting the article with a detection medium for a period of time; and after contacting the article with the detection medium for the period of time, analyzing the detection medium to detect a biological activity of the test microorganisms.

Embodiment AO is a method, comprising:

contacting the article of any one of Embodiments T through AA with a disinfectant in a flow stream for at least a predefined minimum contact time;

after contacting the article with the disinfectant for the minimum contact time period, contacting the article with a rinse solvent that does not comprise the disinfectant;

after contacting the article with the rinse solvent, contacting the article with a detection medium for a period of time; and after contacting the article with the detection medium for the period of time, analyzing the detection medium to detect a biological activity of the test microorganisms.

Embodiment AP is the method of Embodiment AN or Embodiment AO, wherein the effective amount of the disinfectant is a quantity of the disinfectant that is sufficient to render all of the test microorganisms nonviable.

Embodiment AQ is the method of any one of Embodiments AB through AP, wherein the minimum contact time is about 3 minutes to about 90 minutes.

Embodiment AR is the method of any one of Embodiments AB through AQ, wherein contacting the article with the detection medium for a period of time comprises contacting the article with the detection medium for about 5 minutes to about 48 hours.

Embodiment AS is the method of any one of Embodiments AB through AR, wherein analyzing the detection medium to detect a biological activity of the test microorganisms comprises detecting vegetative cells derived from germination of a spore.

Embodiment AT is the method of any one of Embodiments AB through AS, wherein analyzing the detection medium to detect a biological activity of the test microorganisms comprises detecting an enzyme activity of the pores and/or an enzyme activity of vegetative cells derived from germination of a spore.

Embodiment AU is the method of Embodiment AT, wherein detecting an enzyme activity comprises detecting an enzyme activity selected from the list of consisting of phosphatase (e.g., acid phosphatase or alkaline phosphatase) activity, beta-glucosidase activity, alpha-glucosidase activity, cellulase activity, xylanase activity, beta-glucuronidase activity, alpha-glucuronidase activity, alpha-galactosidase activity, beta-galactosidase activity, laccase activity, protease activity, peptidase activity, amylase activity, glucose oxidase activity, lyase activity, esterase activity, lipase activity oxidoreductase activity, and a combination of any two or more of the foregoing enzyme activities.

Embodiment AV is the method of any one of Embodiments AB through AU, wherein contacting the article with the detection medium for a period of time comprises contacting the article with the detection medium at a predefined temperature.

Embodiment AW is the method of any one of Embodiments AB through AF, Embodiments AI through AK, and Embodiment AN; wherein contacting the article with the effective amount of the neutralizer compound comprises contacting the article with the effective amount of the neutralizer compound before contacting the article with the detection medium.

Embodiment AX is the method of any one of Embodiments AB through AF, Embodiments AI through AK, and Embodiment AN; wherein contacting the article with the effective amount of the neutralizer compound comprises contacting the article with the detection medium that comprises the effective amount of the neutralizer compound.

Embodiment AY is the article of any one of the Embodiments A-Q or the process challenge device of any one of the Embodiments T-AA, wherein the cationic nitrogen-containing ligand monomer is of the Formula I.

Embodiment AZ is the article of any one of the Embodiments A-Q or the process challenge device of any one of the Embodiments T-AA, wherein the cationic nitrogen-containing ligand monomer is of the Formula II or IIa.

Embodiment BA is the article of any one of the Embodiments A-Q or the process challenge device of any one of the Embodiments T-AA, wherein the guanidinyl-containing ligand monomer used to make the copolymer comprises 2-(4-guanidinobutylcarbamoylamino)ethyl-2-methylprop-2-enoate.

Embodiment BB is the article of any one of the Embodiments A-Q or the process challenge device of any one of the Embodiments T-AA, wherein the guanidinyl-containing ligand monomer used to make the copolymer comprises 2-(4-guanidinobutylcarbamoylamino)ethyl-2-methylprop-2-enoate hemisulfate.

Embodiment BC is the article of any one of the Embodiments A-Q, wherein the guanidinyl-containing ligand monomer used to make the copolymer comprises 2-(4-guanidinobutylcarbamoylamino)ethyl-2-methylprop-2-enoate hemisulfate, the oxy monomer used to make the copolymer comprises glycidyl methacrylate, and the amide monomer used to make the copolymer comprises N-vinyl pyrrolidone.

Embodiment BD is the article of any one of the Embodiments A-Q or the process challenge device of any one of the Embodiments T-AA, wherein the quaternary ammonium-containing ligand monomer is of the Formula I.

Embodiment BE is the article of any one of the Embodiments A-H or the process challenge device of any one of the Embodiments T-AA, wherein the water-soluble or water-dispersible polymeric binding agent is selected from the group consisting of agarose, polyvinylpyrrolidone, poly(alkylene oxide), polyvinyl alcohol, poly(2-acrylamido-2- methyl-1-propanesulfonic acid), poly(methacrylic acid) and a combination of any two or more of the foregoing polymeric binding agents.

Embodiment BF is the article of any one of the Embodiments A-H or the process challenge device of any one of the Embodiments T-AA, wherein the water-soluble or water-dispersible polymeric binding agent comprises polyvinylpyrrolidone or polyvinyl alcohol.

Embodiment BG is the article of any one of the Embodiments A-H or the process challenge device of any one of the Embodiments T-AA, wherein the water-soluble or water-dispersible polymeric binding agent is polyvinyl alcohol.

Embodiment BH is the article of any one of the Embodiments A-H or the process challenge device of any one of the Embodiments T-AA, wherein the water soluble or water-dispersible polymeric binding agent is selected from an acrylate polymer or a methacrylate polymer substituted with a carboxylic acid group or a sulfonic acid group.

Embodiment BI is the article of any one of the Embodiments A-H or the process challenge device of any one of the Embodiments T-AA, wherein the water soluble or water-dispersible polymeric binding agent is a polysaccharide.

Embodiment BJ is the article of Embodiment J, wherein the bacteria comprises bacteria of a species of Geobacillus.

Embodiment BK is the article of Embodiment J, wherein the bacteria comprises Geobacillus stearothermophilus.

Embodiment BL is the article of Embodiment J, wherein the bacteria comprises Geobacillus stearothermophilus spores.

Embodiment BM is the article of any one of the Embodiments A-S or the process challenge device of any one of the Embodiments T-AA, wherein the plurality of viable test microorganisms consists of about 1000 test microorganisms to about $2 \times 10^5$ test microorganisms.

Embodiment BN is the method of any one of Embodiments AB through AX, further comprising contacting the article of any one of Embodiments A through AA with a sterilant for at least a predefined minimum contact time.

Embodiment BO is a method for preparing an article comprising: a) providing a nonwoven substrate; b) irradiating the substrate with ionizing radiation to provide free radicals on the surface of the substrate; c) imbibing the irradiated substrate with an aqueous monomer mixture comprising a cationic nitrogen-containing ligand monomer, an amide monomer, and an oxy monomer to form a grafted substrate; d) optionally washing and then drying the grafted substrate; e) applying to the grafted substrate an aqueous coating comprising a plurality of test microorganisms to form a coated grafted substrate; f) drying the coating.

Embodiment BP is the method of Embodiment BO, wherein the nonwoven substrate comprises meltblown microfibers of a hydrophobic thermoplastic polyolefin.

Embodiment BQ is the method of any one of the Embodiments BO-BP, wherein the nonwoven substrate is irradiated with e-beam irradiation.

Embodiment BR is the method of any one of the Embodiments BO-BQ, wherein the cationic containing ligand monomer is of the Formula I.

Embodiment BS is the method of any one of the Embodiments BO-BQ, wherein the cationic containing ligand monomer is of the Formula II.

Embodiment BT is the method of any one of the Embodiments BO-BQ, wherein the cationic containing ligand monomer is of the Formula IIIa or IIIb.

Embodiment BU is the method of any one of the Embodiments BO-BQ, wherein the cationic containing ligand monomer is selected from a quaternary ammonium-containing and/or guanidinyl-containing ligand monomer.

Embodiment BV is the method of any one of the Embodiments BO-BU, wherein the dried coating further comprises a water-soluble or water-dispersible polymeric binding agent.

Embodiment BW is the method of Embodiment BV, wherein the water-soluble or water-dispersible polymeric binding agent is selected from the group consisting of agarose, polyvinylpyrrolidone, poly(alkylene oxide), polyvinyl alcohol, poly(2-acrylamido-2-methyl-1-propanesulfonic acid), poly(methacrylic acid) and a combination of any two or more of the foregoing polymeric binding agents.

Embodiment BX is the method of any one of the Embodiments BO-BW, wherein the plurality of test microorganisms comprises bacteria.

Embodiment BY is the method of the Embodiments BO-BW, wherein the plurality of test microorganisms comprises spores.

Embodiment BZ is an article prepared by the method of any one of the Embodiments BO-BY.

Embodiment CA is the method of any one of Embodiments AB through AX and BN, wherein the sterilant comprises a gas plasma, vaporized hydrogen peroxide, ozone, chlorine dioxide, peracetic acid, ethylene oxide or ions derived therefrom.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent. All parts are expressed as parts by weight unless otherwise indicated.

EXAMPLES

Materials

[3-(Methacryloylamino)propyl]trimethylammonium chloride (MAPTAC), resazurin sodium salt, L-serine, and malt extract broth were obtained from the Sigma-Aldrich Corporation, St. Louis, Mo.).

2-(Diethylamino)ethyl methacrylate (DEAEMA) was obtained from Sigma-Aldrich.

N-Vinylpyrrolidone (NVP) was obtained from TCI Americas, Portland, Oreg.

Glycidyl methacrylate (GMA) was obtained from Pfaltz and Bauer, Waterbury, Conn.

Glycine (USP) was obtained from EMD Chemicals Incorporated, Gibbstown, N.J.

4-[2-(methacryloyloxy)ethylaminocarbonylamino]butyl guanidinium hemisulfate (IEMAGM) was prepared according to the procedure described in Example 101 of U.S. Pat. No. 9,272,246.

Preparation of *Aspergillus brasiliensis* Spore Suspension.

Dehydrated Potato Dextrose Agar (PDA) was obtained from Becton, Dickinson and Company (Franklin Lakes, N.J.). The PDA was prepared, sterilized according to the manufacturer's instructions, and acidified to pH 3.5 with tartaric acid. A plurality of PDA plates were inoculated with a suspension of spores (*Aspergillus brasiliensis* ATCC #16404). The inoculated plates were incubated for 14 days at 30° C. After incubation, plates were flooded with a solution of 10% (v/v) glycerol/0.05% TWEEN-20 detergent and the spores were scraped off the agar into the solution using a sterile scraper. Suspensions from each of the plates were pooled into a single spore suspension. Aliquots (1 mL)

of the pooled suspension were pipetted into sterile tubes, which were stored at −80° C. until use. Each aliquot contained approximately 4×10$^8$ spores.

Preparation of Copolymer-Grafted Nonwoven Substrate

The copolymer-grafted nonwoven substrate was prepared from a melt-blown polypropylene microfiber (PP) nonwoven substrate (characterized by an effective fiber diameter of 4.3 micrometers, a basis weight of 105 grams per square meter, and solidity of 10%) according to the general procedure reported in example 1 of U.S. Patent Application Publication No. 2015/0099413, incorporated herein by reference in its entirety. Specifically, a 12.7 cm by 12.7 cm sample of the melt-blown polypropylene microfiber nonwoven substrate was purged of air under a nitrogen atmosphere in a glove box and inserted into a plastic bag and sealed. The sealed bag was then removed from the glove box and irradiated to a dose level of 40 kGy by passing through an Energy Sciences, Inc. 'Electrocurtain' CB-300 electron beam in a single pass operation at a web speed of approximately 5.5 meters/minute and an accelerating voltage of 300 kV. The sealed bag was returned to the nitrogen atmosphere controlled glove box where the nonwoven material was imbibed with 23 grams of a nitrogen purged imbibing solution and the bag resealed after expelling most of the nitrogen. During this step the oxygen level in the glove box was generally maintained below 50 parts per million (ppm). The sample was maintained flat in the bag and evenly saturated for at least 12 hours. The imbibing solution was prepared in deionized water with 26.6% by weight total mixed monomers NVP/GMA/MAPTAC. The individual monomer concentrations were 12.5% NVP, 4.1% GMA, and 10% MAPTAC.

The resulting copolymer grafted nonwoven substrate was removed from the bag and boiled in deionized water for one hour. The substrate was removed from the water bath and air dried at room temperature for 24 hours. The substrate material was weighed before and after the procedure to determine the amount of copolymer material grafted to the substrate. The weight gain by the substrate following grafting was about 280% of the original weight of the substrate. This substrate (about 1 mm thick sheet) was used to prepare the articles (hereinafter, "discs") described in the Examples.

Example 1

Preparation of Article

A 4% solution of agarose (melting temperature less than 65° C., catalog number A2790, available from Sigma-Aldrich Corporation) was prepared by adding the agarose to sterile, deionized water and heating in a microwave until dissolved. The agarose solution was then cooled to approximately 40° C. and diluted by adding with a pipet an equal volume of the *Aspergillus brasiliensis* spore suspension (described above). Following the dilution step, the final agarose content of the resulting coating suspension was 2% and the spore concentration was about 2×10$^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about 2×10$^6$ spores.

Example 2

A 2% solution of agarose (melting temperature less than 65° C., catalog number A2790, available from Sigma-Aldrich Corporation) was prepared by adding the agarose to sterile, deionized water and heating in a microwave until dissolved. The agarose solution was then cooled to approximately 40° C. and diluted by adding with a pipet an equal volume of the *Aspergillus brasiliensis* spore suspension (described above). Following the dilution step, the final agarose content of the resulting coating suspension was 1% and the spore concentration was about 2×10$^8$ spores/mL. The coating suspension (10 microliters) was then spotted using a pipet onto either a 7 mm diameter circular disc or onto a 15.2 cm by 15.2 cm sheet of the copolymer grafted nonwoven substrate (described above). The spotted substrate was air dried overnight at room temperature. For the spotted sheet, sterile scissors were used to cut-out a 1 cm by 1 cm square shaped disc with the dried, spore-coated section positioned at the center of the disc. Each disc was loaded with about 2×10$^6$ spores.

Example 2a

Discs were prepared following the procedure of Example 2 with the exception that agarose was not included in the solution used to spot the substrate with spores. Specifically for Example 2a, the copolymer grafted nonwoven substrate of Example 1 was spotted with 10 microliters of an aqueous suspension containing of glycerol (5% v/v) and Tween 20 detergent (0.025 v/v), and spores at a concentration of 2×10$^8$ spores/mL. The spotted substrate was air dried overnight at room temperature. Sterile scissors were used to cut-out a 1 cm by 1 cm square shaped disc with the dried, spore-coated section positioned at the center of the disc. Each disc was loaded with about 2×10$^6$ spores.

Example 3

A 1% solution of agarose (melting temperature less than 65° C., catalog number A2790, available from Sigma-Aldrich Corporation) was prepared by adding the agarose to sterile, deionized water and heating in a microwave until dissolved. The agarose solution was then cooled to approximately 40° C. and diluted by adding with a pipet an equal volume of the *Aspergillus brasiliensis* spore suspension (described above). Following the dilution step, the final agarose content of the resulting coating suspension was 0.5% and the spore concentration was about 2×10$^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about 2×10$^6$ spores.

Example 4

A 0.5% solution of agarose (melting temperature less than 65° C., catalog number A2790, available from Sigma-Aldrich Corporation) was prepared by adding the agarose to sterile, deionized water and heating in a microwave until dissolved. The agarose solution was then cooled to approximately 40° C. and diluted by adding with a pipet an equal volume of the *Aspergillus brasiliensis* spore suspension (described above). Following the dilution step, the final agarose content of the resulting coating suspension was 0.25% and the spore concentration was about 2×10$^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about $2 \times 10^6$ spores.

Example 5

A 4% solution of PEG 20K (polyethylene glycol with an average MW 20,000, catalog number 81300, available from Sigma-Aldrich Corporation) in sterile, deionized water was added to an equal volume of the *Aspergillus brasiliensis* spore suspension described above. Following the dilution step, the final PEG 20K content of the resulting coating suspension was 2% and the spore concentration was about $2 \times 10^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about $2 \times 10^6$ spores.

Example 6

A 2% solution of PEG 20K (polyethylene glycol with an average MW 20,000, catalog number 81300, available from Sigma-Aldrich Corporation) in sterile, deionized water was added to an equal volume of the *Aspergillus brasiliensis* spore suspension described above. Following the dilution step, the final PEG 20K content of the resulting coating suspension was 1% and the spore concentration was about $2 \times 10^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about $2 \times 10^6$ spores.

Example 7

A 1% solution of PEG 20K (polyethylene glycol with an average MW 20,000, catalog number 81300, available from Sigma-Aldrich Corporation) in sterile, deionized water was added to an equal volume of the *Aspergillus brasiliensis* spore suspension described above. Following the dilution step, the final PEG 20K content of the resulting coating suspension was 0.5% and the spore concentration was about $2 \times 10^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about $2 \times 10^6$ spores.

Example 8

A 0.5% solution of PEG 20K (polyethylene glycol with an average MW 20,000, catalog number 81300, available from Sigma-Aldrich Corporation) in sterile, deionized water was added to an equal volume of the *Aspergillus brasiliensis* spore suspension described above. Following the dilution step, the final PEG 20K content of the resulting coating suspension was 0.25% and the spore concentration was about $2 \times 10^8$ spores/mL. The coating suspension (10 microliters) was then spotted using a pipet onto a 7 mm diameter circular disc that had been punched from the copolymer grafted nonwoven substrate (described above). The spotted substrate was air dried overnight at room temperature. Each disc was loaded with about $2 \times 10^6$ spores.

Example 9

Discs from Example 1 were individually placed in wells of a polystyrene 48-well culture plate that was incubated at 25° C. in a water bath. The discs were pre-wetted with 20 microliters of sterile, deionized water. Four hundred microliters of ortho-phthalaldehyde (OPA) solution (Rapicide OPA28 High-Level Disinfectant available from Medivators Company, Minneapolis, Minn.) at the minimum effective concentration (diluted to 0.35% OPA using sterile, deionized water) was pipetted onto each disc. The plate was maintained at 25° C. for 5 minutes and then 600 microliters of glycine (6 g/L in sterile, deionized water) was added to each well. The plate was incubated at room temperature for an additional 15 minutes. Following the incubation period, sterile forceps were used to transfer each disk to a new well in a second polystyrene 48-well culture plate. Each well of the second plate contained malt extract broth (600 microliters, pH 7.5), supplemented with L-serine (1 mM) and resazurin sodium salt (0.03 mg/mL). The plate was sealed with PARAFILM® M plastic paraffin film and incubated at 37° C. for 21 days.

The wells were checked for outgrowth on days 2, 5, 7, 14, and 21 by visually examining the wells for color change of the resazurin indicator and turbidity of the solution. Clear or pink solutions with turbidity were positive for outgrowth. Purple solutions without turbidity were negative for outgrowth.

Positive control wells were prepared using discs that had not been exposed to the OPA solution. Negative control wells were prepared by not adding a disc to the well. The results are reported in Table 1.

Example 10

The same procedure as reported for Example 9 was followed using discs of Example 2 in place of discs of Example 1. A total of 10 discs were evaluated and the results are reported in Table 1.

Example 11

The same procedure as reported for Example 9 was followed using discs of Example 3 in place of discs of Example 1. A total of 10 discs were evaluated and the results are reported in Table 1.

Example 12

The same procedure as reported for Example 9 was followed using discs of Example 4 in place of discs of Example 1. A total of 10 discs were evaluated and the results are reported in Table 1.

Example 13

The same procedure as reported for Example 9 was followed using discs of Example 5 in place of discs of Example 1. A total of 10 discs were evaluated and the results are reported in Table 2.

Example 14

The same procedure as reported for Example 9 was followed using discs of Example 6 in place of discs of Example 1. A total of 10 discs were evaluated and the results are reported in Table 2.

Example 15

The same procedure as reported for Example 9 was followed using discs of Example 7 in place of discs of Example 1. A total of 10 discs were evaluated and the results are reported in Table 2.

Example 16

The same procedure as reported for Example 9 was followed using discs of Example 8 in place of discs of Example 1. A total of 10 discs were evaluated and the results are reported in Table 2.

TABLE 1

Survival of Test Microorganisms after 5-minute exposure to OPA.

| Disc | | Concentration of Agarose in the Coating Suspension | Percentage of Wells (n = 10) Indicating Outgrowth During Incubation | | | | |
|---|---|---|---|---|---|---|---|
| | Preparation | | Day 2 | Day 5 | Day 7 | Day 14 | Day 21 |
| Example 9 | Example 1 | 2% | 0% | 0% | 0% | 0% | 0% |
| Example 10 | Example 2 | 1% | 0% | 0% | 0% | 0% | 0% |
| Example 11 | Example 3 | 0.5% | 0% | 0% | 0% | 10% | 10% |
| Example 12 | Example 4 | 0.25% | 0% | 0% | 0% | 0% | 0% |

TABLE 2

Survival of Test Microorganisms after 5-minute exposure to OPA.

| Disc | | Concentration of PEG 20K in the Coating Suspension | Percentage of Wells (n = 10) Indicating Outgrowth During Incubation | | | | |
|---|---|---|---|---|---|---|---|
| | Preparation | | Day 2 | Day 5 | Day 7 | Day 14 | Day 21 |
| Example 13 | Example 5 | 2% | 0% | 0% | 0% | 0% | 10% |
| Example 14 | Example 6 | 1% | 0% | 0% | 0% | 0% | 10% |
| Example 15 | Example 7 | 0.5% | 0% | 0% | 0% | 0% | 0% |
| Example 16 | Example 8 | 0.25% | 0% | 0% | 0% | 0% | 0% |

Example 17

Individual discs from Example 2 were immersed in a beaker containing 450 mL of a minimum effective concentration (i.e., 0.35%) of ortho-phthalaldehyde (OPA) solution (Rapicide OPA28 High-Level Disinfectant, available from Medivators Company, Minneapolis, Minn.) at 25° C. for variable exposure times (either 2 seconds, 30 seconds, 1 minute, 2 minutes, 3 minutes, 4 minutes, or 5 minutes). A total of ten discs were evaluated for each exposure time. Immediately after the exposure time, the discs were removed from the OPA solution, excess liquid was removed from the discs by gentle shaking, and the discs were transferred to a beaker containing 250 mL of neutralizing solution (6% glycine in sterile, deionized water). The discs were maintained in the neutralization solution for 5 minutes. Each disc was then transferred using sterile forceps to a 15 mL screw-cap conical tube that contained a solution of resazurin (0.03 mg/mL) in 3 mL of malt extract broth at a pH of 7.5. Each tube was incubated at 37° C. for 14 days. The tubes were checked for outgrowth on days 2, 5, 7, and 14 by visually examining the tubes for color change of the resazurin indicator and turbidity of the solution. Clear or pink solutions with turbidity were positive for outgrowth. Purple solutions without turbidity were negative for outgrowth. Positive control tubes were prepared using discs that had not been exposed to the OPA solution. Negative control tubes were prepared by not adding a disc to the tube. The results are reported in Table 3. On day 1, outgrowth was observed for all discs exposed to the OPA solution for up to 30 seconds, while outgrowth was not observed for discs exposed to OPA for 2 minutes or more. The results observed on day 1 remained constant through day 14 for all exposure times except the 1 minute exposure time.

TABLE 3

OPA Treated Discs Coated with Agarose Polymeric binding agent

| Exposure Time to OPA Solution | Percentage of Tubes (n = 10) Indicating Outgrowth During Incubation | | | |
|---|---|---|---|---|
| | Day 1 | Day 5 | Day 7 | Day 14 |
| 2 seconds | 100% | 100% | 100% | 100% |
| 30 seconds | 100% | 100% | 100% | 100% |
| 1 minute | 20% | 40% | 40% | 50% |
| 2 minutes | 0% | 0% | 0% | 0% |
| 3 minutes | 0% | 0% | 0% | 0% |
| 4 minutes | 0% | 0% | 0% | 0% |
| 5 minutes | 0% | 0% | 0% | 0% |
| Positive Control (No exposure to OPA) | 100% | 100% | 100% | 100% |
| Negative Control (No disc added to tube) | 0% | 0% | 0% | 0% |

Example 18

The same procedure as reported in Example 17 was followed with the exception that discs were only evaluated following two exposure times (2 seconds and 5 minutes) and the number of discs evaluated at each time point was increased from 10 discs to 60 discs. All 60 discs exposed to the OPA solution for 2 seconds were positive for outgrowth on all test dates. All 60 discs exposed to the OPA solution for 5 minutes were negative for spore growth on all test dates.

Example 19

A disc from Example 2 was added to a first microcentrifuge tube (1.5 mL) that contained 1 mL of Butterfield's buffer (available from 3M Company, St. Paul, Minn.). The disc was washed with buffer using the following 3-step procedure and the wash buffer was recovered from each wash step. The first tube was vortexed on the high speed setting for 1 minute using a Vortex-Genie 2 mixer (available from Scientific Industries, Bohemia, N.Y.). The disc was removed from the buffer solution of the first tube using sterile forceps and transferred to a second microcentrifuge tube (1.5 mL) that contained fresh Butterfield's buffer. The second tube was vortexed on the high speed setting for 1 minute. The disc was then removed from the buffer solution of the second tube using sterile forceps and transferred to a third microcentrifuge tube (1.5 mL) that contained fresh Butterfield's buffer. The third tube was vortexed on the high speed setting for 1 minute and then the disc was removed using sterile forceps. The recovered buffer solutions from the first, second, and third microcentrifuge tubes were each serially diluted in Butterfield's buffer and separately plated onto PETRIFILM™ Rapid Yeast and Mold Count Plates (available from 3M Company, St. Paul, Minn.). The plates were incubated at 30° C. for 48 hours and colonies were counted by visual examination.

The procedure was repeated using the discs of Example 2a. Each disc type was measured in duplicate. The results are presented in Table 4 with values adjusted based on number of dilutions required. The data shows that based on colony counts, significantly fewer spores (about 100 fold fewer spores) were washed from the disc of Example 2 than from the disc of Example 2a when Butterfield's buffer solution was used as the wash solution. The mean percentage loss of spores from washing discs of Example 2 was only 0.018%, while the mean percentage loss of spores from washing discs of Example 2a was 1.4%.

TABLE 4

|  | Colony count from 1st Wash | Colony Count from 2nd Wash | Colony Count from 3rd Wash | Total of Colony Counts from 3 Washes |
|---|---|---|---|---|
| Example 2 Disc | 123 | 73 | 88 | 284 |
| Example 2 Disc | 43 | 225 | 160 | 428 |
| Example 2a Disc | 8,750 | 5,650 | 4,000 | 18,400 |
| Example 2a Disc | 28,300 | 7,400 | 1,850 | 37,550 |

Example 20

A neutralized OPA solution was prepared by adding glycine in sterile, deionized water to a full strength OPA solution (0.575% OPA, available as Rapicide OPA28 High-Level Disinfectant, Medivators Company) so that the final glycine concentration was 88 mM. The neutralized OPA solution served as the wash solution.

A disc from Example 2 was added to a first microcentrifuge tube (1.5 mL) that contained 1 mL of wash solution. The disc was washed with neutralized OPA solution using the following 3-step procedure and the wash solution was recovered from each wash step. The first tube was vortexed on the high speed setting for 1 minute using a Vortex-Genie 2 mixer. The disc was removed from the wash solution of the first tube using sterile forceps and transferred to a second microcentrifuge tube (1.5 mL) that contained fresh wash solution. The second tube was vortexed on the high speed setting for 1 minute. The disc was then removed from the wash solution of the second tube using sterile forceps and transferred to a third microcentrifuge tube (1.5 mL) that contained fresh wash solution. The third tube was vortexed on the high speed setting for 1 minute and then the disc was removed using sterile forceps. The recovered wash solutions from the first, second, and third microcentrifuge tubes were each serially diluted using Butterfield's Buffer and separately plated onto PETRIFILM™ Rapid Yeast and Mold Count Plates. The plates were incubated at 30° C. for 48 hours and colonies were counted by visual examination.

The procedure was repeated using the discs of Example 2a. Each disc type was measured in duplicate. The results are presented in Table 5 with values adjusted based on number of dilutions required. The data shows that based on colony counts, significantly fewer spores (about 100 fold fewer spores) were washed from the disc of Example 2 than from the disc of Example 2a when the neutralized OPA solution was used as the wash solution. The mean percentage loss of spores from washing discs of Example 2 was only 0.03%, while the mean percentage loss of spores from washing discs of Example 2a was 2.7%.

TABLE 5

|  | Colony count from 1st Wash | Colony Count from 2nd Wash | Colony Count from 3rd Wash | Total of Colony Counts from 3 Washes |
|---|---|---|---|---|
| Example 2 Disc | 485 | 478 | 145 | 1,108 |
| Example 2 Disc | 50 | 40 | 30 | 120 |
| Example 2a Disc | 38,300 | 19,000 | 13,500 | 70,800 |
| Example 2a Disc | 19,000 | 14,500 | 5,900 | 39,400 |

Example 21

Process challenge devices similar to the device 300 of FIG. 5 (with the exceptions that they did not include the reservoir, the frangible container, the conduit, or the second compartment) were constructed. Each device was a molded, semi-transparent ABS (acrylonitrile butadiene styrene) plastic card generally rectangular shaped with external dimensions of about 6.0 cm in length, 5.1 cm in width, and 1.5 mm in thickness. The total length of the microfluidic channel was about 12.7 cm and the channel cross section was about 1.0 mm by about 1.5 mm.

A 7 mm diameter coated disc from Example 2 was placed (secured with a small amount of adhesive) in the circular cavity section located in the liquid flow path of the channel A clear, PET film (10 mm thick) was adhesively laminated to the device so as to seal a top cover over the channel.

The process challenge device was engaged into a manifold assembly that connected the liquid outlet port of a Medivators DSD-201 Automatic Endoscope Reprocessor (AER) (available from Medivators Company, Minneapolis, Minn.) to the inlet port of the process challenge device and the outlet port of the process challenge device to an endoscope that was attached to the AER. This allowed the fluids of the disinfection cycle to be circulated through the entire length of the microfluidic channel, including through the disc. The disinfection cycle was at 25° C. and consisted of four ordered steps: a pre-rinse with water for 30 seconds, an OPA solution flush and soak for 5 minutes, two water rinse cycles, and finally a pulsed isopropyl alcohol/water flush.

At the completion of the disinfection cycle, the process challenge device was detached from the AER instrument and 320 microliters of sterile detection medium was delivered via the inlet port of the process challenge device so that it contacted the spore coated disc. The detection medium was a malt extract broth (15 g/L, pH 7.5) supplemented with glycine (15 g/L), L-serine (0.1 g/L), and resazurin sodium salt (0.03 g/L). The device was then incubated at 37° C. for 7 days. Following the incubation period, the devices were checked for outgrowth by visually examining the detection medium for color change of the resazurin indicator and for turbidity. Clear or pink solutions with turbidity were positive for outgrowth. Purple solutions without turbidity were negative for outgrowth. Positive control devices were prepared by using fresh devices that had not been exposed to a disinfection cycle. A total of 4 devices were submitted to the disinfection procedure and all 4 devices tested negative for outgrowth.

Example 22

A 10.2 cm by 10.2 cm sample of melt-blown polypropylene microfiber nonwoven substrate about 1 mm thick (characterized by an effective fiber diameter of 4.2 micrometers and a basis weight of 105 grams per square meter) was purged of air under a nitrogen atmosphere for 10 minutes in a glove box and inserted into a plastic bag and sealed. The sealed bag was then removed from the glove box and irradiated to a dose level of 70 kGy by passing through an Energy Sciences, Inc. 'Electrocurtain' CB-300 electron beam in a single pass operation at a web speed of approximately 5.5 meters/minute and an accelerating voltage of 300 kV. The sealed bag was returned to the nitrogen atmosphere controlled glove box where the nonwoven material was imbibed with 13 grams of a nitrogen purged imbibing solution and the bag resealed after expelling most of the nitrogen. A roller was used to uniformly distribute the imbibing solution to the substrate. The sample was maintained flat in the bag and evenly saturated for 24 hours. The imbibing solution was prepared in deionized water with 21.5% by weight total mixed monomers NVP/GMA/IEMAGM. The individual monomer concentrations were 12.5% NVP, 4% GMA, and 5% IEMAGM.

The resulting copolymer grafted nonwoven substrate was removed from the bag and washed with agitation for 20 minutes in 800 mL of a saline solution. The saline wash step was followed with three washes of the substrate using warm distilled water. Fresh water was used in each wash step. A final wash was conducted using warm water for 20 minutes. The washed substrate was air dried overnight. The substrate material was weighed both before and after the procedure to determine the amount of copolymer material grafted to the substrate. The weight gain by the substrate following grafting was about 289% of the original weight of the substrate.

Example 23

The same procedure as described in Example 22 for preparation of a copolymer grafted nonwoven substrate was followed with the exception that the individual monomer concentrations were 12.5% NVP, 4% GMA, and 2.5% IEMAGM. The weight gain by the substrate following grafting was about 288% of the original weight of the substrate.

Example 24

The same procedure as described in Example 22 for preparation of a copolymer grafted nonwoven substrate was followed with the exception that the imbibing solution was prepared in deionized water with 21.5% by weight total mixed monomers NVP/GMA/2-(diethylamino)ethyl methacrylate (DEAEMA). The individual monomer concentrations were 12.5% NVP, 4% GMA, and 5% DEAEMA. The weight gain by the substrate following grafting was about 316% of the original weight of the substrate.

Example 25

The same procedure as described in Example 24 for preparation of a copolymer grafted nonwoven substrate was followed with the exception that the individual monomer concentrations were 12.5% NVP, 4% GMA, and 2.5% DEAEMA. The weight gain by the substrate following grafting was about 275% of the original weight of the substrate.

Example 26

A 2% solution of polyvinylpyrrolidone (PVP) (average MW 96,000, available from Alfa Aesar Company, Haverhill, Mass.) in sterile, deionized water was added to an equal volume of *Aspergillus brasiliensis* spore suspension ($1 \times 10^8$ spores/mL). Following the dilution step, the final PVP content of the resulting coating suspension was 1% and the spore concentration was about $5 \times 10^7$ spores/mL. The coating suspension (10 microliters) was then spotted using a pipet onto a 7 mm diameter circular disc that had been punched from the copolymer grafted nonwoven substrate of Example 22. The spotted substrate was air dried overnight at room temperature. Each disc was loaded with about $5 \times 10^5$ spores.

Example 27

The same procedure as described in Example 26 was followed with the exception that the disc was punched from the copolymer grafted nonwoven substrate of Example 23. Each disc was loaded with about $5 \times 10^5$ spores.

Example 28

The same procedure as described in Example 26 was followed with the exception that the disc was punched from the copolymer grafted nonwoven substrate of Example 24. Each disc was loaded with about $5 \times 10^5$ spores.

Example 29

The same procedure as described in Example 26 was followed with the exception that the disc was punched from the copolymer grafted nonwoven substrate of Example 25. Each disc was loaded with about $5 \times 10^5$ spores.

Example 30

A 2% solution of polyvinyl alcohol (PVA) (average MW 96,000, available from Alfa Aesar Company) in sterile, deionized water was added to an equal volume of the *Aspergillus brasiliensis* spore suspension ($1 \times 10^8$ spores/mL). Following the dilution step, the final PVA content of the resulting coating suspension was 1% and the spore concentration was about $5 \times 10^7$ spores/mL. The coating suspension (10 microliters) was then spotted using a pipet onto either a 5 mm or 7 mm diameter circular disc that had been punched from the copolymer grafted nonwoven substrate of Example 22. The spotted substrate was air dried overnight at room temperature. Each disc was loaded with about $5 \times 10^5$ spores.

Example 31

The same procedure as described in Example 30 was followed with the exception that the disc was punched from the copolymer grafted nonwoven substrate of Example 23. Each disc was loaded with about $5 \times 10^5$ spores.

Example 32

The same procedure as described in Example 30 was followed with the exception that the disc was punched from the copolymer grafted nonwoven substrate of Example 24. Each disc was loaded with about $5 \times 10^5$ spores.

Example 33

The same procedure as described in Example 30 was followed with the exception that the disc was punched from the copolymer grafted nonwoven substrate of Example 25. Each disc was loaded with about $5 \times 10^5$ spores.

Example 34

A 10 microliter suspension of *Aspergillus brasiliensis* spores ($5 \times 10^7$ spores/mL) was spotted directly onto either a 5 mm or 7 mm circular disc that had been punched from the copolymer grafted nonwoven substrate of Example 22. The spotted substrate was air dried overnight at room temperature. Each disc was loaded with about $5 \times 10^5$ spores.

Example 35

The same procedure as described in Example 34 was followed with the exception that the disc was punched from the copolymer grafted nonwoven substrate of Example 23. Each disc was loaded with about $5 \times 10^5$ spores.

Example 36

The same procedure as described in Example 34 was followed with the exception that the disc was punched from the copolymer grafted nonwoven substrate of Example 24. Each disc was loaded with about $5 \times 10^5$ spores.

Example 37

The same procedure as described in Example 34 was followed with the exception that the disc was punched from the copolymer grafted nonwoven substrate of Example 25. Each disc was loaded with about $5 \times 10^5$ spores.

Example 38

The same procedure as described in Example 22 for preparation of a copolymer grafted nonwoven substrate was followed with the exception that the imbibing solution was prepared in deionized water with 21.5% by weight total mixed monomers NVP/GMA/MAPTAC. The individual monomer concentrations were 12.5% NVP, 4% GMA, and 5% MAPTAC. The weight gain by the substrate following grafting was about 309% of the original weight of the substrate.

Example 39

The same procedure as described in Example 22 for preparation of a copolymer grafted nonwoven substrate was followed with the exception that the individual monomer concentrations were 12.5% NVP, 4% GMA, and 2.5% MAPTAC. The weight gain by the substrate following grafting was about 302% of the original weight of the substrate.

Example 40

A 2% solution of polyvinylpyrrolidone (PVP) (average MW 96,000, available from Alfa Aesar Company) in sterile, deionized water was added to an equal volume of the *Aspergillus brasiliensis* spore suspension ($1 \times 10^8$ spores/mL). Following the dilution step, the final PVP content of the resulting coating suspension was 1% and the spore concentration was about $5 \times 10^8$ spores/mL. The coating suspension (10 microliters) was then spotted using a pipet onto a 7 mm diameter circular disc that had been punched from the copolymer grafted nonwoven substrate of Example 38. The spotted substrate was air dried overnight at room temperature. Each disc was loaded with about $5 \times 10^5$ spores.

Example 41

The same procedure as described in Example 40 was followed with the exception that the disc was punched from the copolymer grafted nonwoven substrate of Example 39. Each disc was loaded with about $5 \times 10^5$ spores.

Example 42

A 2% solution of polyvinyl alcohol (PVA) (average MW 96,000, available from Alfa Aesar Company) in sterile, deionized water was added to an equal volume of the *Aspergillus brasiliensis* spore suspension ($1 \times 10^8$ spores/mL). Following the dilution step, the final PVA content of the resulting coating suspension was 1% and the spore concentration was about $5 \times 10^7$ spores/mL The coating suspension (10 microliters) was then spotted using a pipet onto either a 5 mm or 7 mm diameter circular disc that had been punched from the copolymer grafted nonwoven substrate of Example 38. The spotted substrate was air dried overnight at room temperature. Each disc was loaded with about $5 \times 10^5$ spores.

Example 43

The same procedure as described in Example 42 was followed with the exception that the disc was punched from the copolymer grafted nonwoven substrate of Example 39. Each disc was loaded with about $5 \times 10^5$ spores.

Example 44

A 10 microliter suspension of *Aspergillus brasiliensis* spores ($5 \times 10^7$ spores/mL) was spotted directly onto either a 5 mm or 7 mm circular disc that had been punched from the copolymer grafted nonwoven substrate of Example 38. The spotted substrate was air dried overnight at room temperature. Each disc was loaded with about $5 \times 10^5$ spores.

Example 45

The same procedure as described in Example 44 was followed with the exception that the disc was punched from the copolymer grafted nonwoven substrate of Example 39. Each disc was loaded with about $5 \times 10^5$ spores.

Example 46

Discs prepared using the procedures of Examples 26-37 and 40-45 were individually placed in separate tubes that contained 9 mL of Butterfield's buffer. Each tube was vortexed on the high speed setting for one minute. The disc was removed and the recovered buffer solution was serially diluted in Butterfield's buffer and plated onto PETRIFILM™ Rapid Yeast and Mold Count Plates (available from 3M Company, St. Paul, Minn.). The plates were incubated at 37° C. for 48 hours and colonies were counted by visual examination. A total of three discs of each type were analyzed. Based on the number of colonies counted, the percentage of spores washed from each disc was calculated. The mean results are presented in Table 6 with values adjusted based on number of dilutions required.

TABLE 6

| Disc of Example | Binding Agent | Monomer Units of Copolymer | Percentage of Spores Removed from the Disc by Washing |
|---|---|---|---|
| 26 | PVP | NVP/GMA/5% IEMAGM | 1.6 |
| 30 | PVA | NVP/GMA/5% IEMAGM | 0.1 |
| 34 | none | NVP/GMA/5% IEMAGM | 3.2 |
| 27 | PVP | NVP/GMA/2.5% IEMAGM | 0.9 |
| 31 | PVA | NVP/GMA/2.5% IEMAGM | 0.3 |
| 35 | none | NVP/GMA/2.5% IEMAGM | 0.3 |
| 40 | PVP | NVP/GMA/5% MAPTAC | 0.03 |
| 42 | PVA | NVP/GMA/5% MAPTAC | 0.01 |
| 44 | none | NVP/GMA/5% MAPTAC | 0.02 |
| 41 | PVP | NVP/GMA/2.5% MAPTAC | 0.03 |
| 43 | PVA | NVP/GMA/2.5% MAPTAC | 0.02 |
| 45 | none | NVP/GMA/2.5% MAPTAC | 0.04 |
| 28 | PVP | NVP/GMA/5% DEAEMA | 1.5 |
| 32 | PVA | NVP/GMA/5% DEAEMA | 0.6 |
| 36 | none | NVP/GMA/5% DEAEMA | 2.1 |
| 29 | PVP | NVP/GMA/2.5% DEAEMA | 1.2 |
| 33 | PVA | NVP/GMA/2.5% DEAEMA | 0.2 |
| 37 | none | NVP/GMA/2.5% DEAEMA | 4.3 |

Example 47

A 2% solution of poly(2-acrylamido-2-methyl-1-propanesulfonic acid) (PAMPS) (average MW 9,500, available from Sigma-Aldrich Corporation) in sterile, deionized water was added to an equal volume of the *Aspergillus brasiliensis* spore suspension ($1 \times 10^8$ spores/mL). Following the dilution step, the final PVP content of the resulting coating suspension was 1% and the spore concentration was about $5 \times 10^7$ spores/mL. The coating suspension (10 microliters) was then spotted using a pipet onto a 7 mm diameter circular disc that had been punched from the copolymer grafted nonwoven substrate of Example 38. The spotted substrate was air dried overnight at room temperature. Each disc was loaded with about $5 \times 10^5$ spores.

Example 48

A 2% solution of poly(methacrylic acid, sodium salt) (PMMA) (average MW 2,000,000, available from Sigma-Aldrich Corporation) in sterile, deionized water was added to an equal volume of the *Aspergillus brasiliensis* spore suspension ($1 \times 10^8$ spores/mL). Following the dilution step, the final PVP content of the resulting coating suspension was 1% and the spore concentration was about $5 \times 10^7$ spores/mL. The coating suspension (10 microliters) was then spotted using a pipet onto a 7 mm diameter circular disc that had been punched from the copolymer grafted nonwoven substrate of Example 38. The spotted substrate was air dried overnight at room temperature. Each disc was loaded with about $5 \times 10^5$ spores.

Example 49

A 2% solution of agarose (melting temperature less than 65° C., catalog number A2790, available from Sigma-Aldrich Corporation) was prepared by adding the agarose to sterile, deionized water and heating in a microwave until dissolved. The agarose solution was then cooled to approximately 40° C. and diluted by adding with a pipet an equal volume of the *Aspergillus brasiliensis* spore suspension ($1 \times 10^8$ spores/mL). Following the dilution step, the final agarose content of the resulting coating suspension was 1% and the spore concentration was about $5 \times 10^7$ spores/mL. The coating suspension (10 microliters) was then spotted using a pipet onto a 7 mm diameter circular disc that had been punched from the copolymer grafted nonwoven substrate of Example 38. The spotted substrate was air dried overnight at room temperature. Each disc was loaded with about $5 \times 10^5$ spores.

Example 50

Discs prepared using the procedures of Examples 40, 42, 44, and 47-49 were individually placed in separate tubes that contained 9 mL of Butterfield's buffer. Each tube was vortexed on the high speed setting for one minute. The disc was removed and the recovered buffer solution was serially diluted in Butterfield's buffer and plated onto PETRIFILM™ Rapid Yeast and Mold Count Plates. The plates were incubated at 37° C. for 44 hours and colonies were counted by visual examination. A total of three discs of each type were analyzed. Based on the number of colonies counted, the percentage of spores washed from each disc was calculated. The mean results are presented in Table 7 with values adjusted based on number of dilutions required.

TABLE 7

| Disc of Example | Binding Agent | Monomer Units of Copolymer | Percentage of Spores Removed from the Disc by Washing |
|---|---|---|---|
| 40 | PVP | NVP/GMA/5% MAPTAC | 0.008 |
| 42 | PVA | NVP/GMA/5% MAPTAC | 0.006 |
| 47 | PAMPS | NVP/GMA/5% MAPTAC | 0.014 |

TABLE 7-continued

| Disc of Example | Binding Agent | Monomer Units of Copolymer | Percentage of Spores Removed from the Disc by Washing |
|---|---|---|---|
| 48 | PMAA | NVP/GMA/5% MAPTAC | 0.052 |
| 49 | agarose | NVP/GMA/5% MAPTAC | 0.072 |
| 44 | none | NVP/GMA/5% MAPTAC | 0.070 |

Example 51

Discs from Examples 30-37, 42-43, and 44-45 were individually placed in wells of polystyrene 48-well culture plates (five of the 5 mm circular discs were evaluated from each Example). The discs were pre-wetted by adding 20 microliters of sterile, deionized water to each well and the plates were then incubated at 25° C. for 10 minutes in a water bath. Four hundred microliters of ortho-phthalaldehyde (OPA) solution (Rapicide OPA28 High-Level Disinfectant available from Medivators Company, Minneapolis, Minn.) at a concentration of 0.55% OPA was pipetted onto each disc. The plate was maintained at 25° C. for 5 minutes and then 600 microliters of glycine (88 mM in sterile, deionized water) was added to each well. The plate was incubated at room temperature for an additional 5 minutes. Following the incubation period, sterile forceps were used to transfer each disk to a new well in a second set of polystyrene 48-well culture plates. Each well in the second plates contained 800 microliters malt extract broth (pH 7.5, available from Sigma-Aldrich Corporation, catalog #M6409) that was supplemented with 0.03 mg/mL of resazurin sodium salt. The plates were sealed with PARAFILM® M plastic paraffin film and incubated at 37° C. for 7 days.

The wells were checked for outgrowth on days 1, 5, and 7 by visually examining the wells for color change of the resazurin indicator and turbidity of the solution. Clear or pink solutions with turbidity were positive for outgrowth. Purple solutions without turbidity were negative for outgrowth. Positive control wells were prepared using discs that had not been exposed to the OPA solution. Negative control wells were prepared by not adding a disc to the well. All of the positive control wells showed outgrowth on days 1, 5 and 7. None of the negative control wells showed outgrowth on days 1, 5, and 7. The results are reported in Table 8.

Example 52

A stock suspension of *Geobacillus stearothermophilus* was diluted with Butterfield's buffer to obtain a spore concentration of $4\times10^8$ spores/mL. A 2% solution of polyvinyl alcohol (PVA) (average MW 96,000, available from Alfa Aesar Company) in sterile, deionized water was added to an equal volume of the *Geobacillus stearothermophilus* spore suspension. Following the dilution step, the final PVA content of the resulting coating suspension was 1% and the spore concentration was about $2\times10^8$ spores/mL. The coating suspension (10 microliters) was then spotted using a pipet onto a 5 mm diameter circular disc that had been punched from the copolymer grafted nonwoven substrate of Example 38. The spotted substrate was air dried overnight at room temperature. Each disc was loaded with about $2\times10^6$ spores.

Example 53

A 10 microliter suspension of *Geobacillus stearothermophilus* spores ($2\times10^8$ spores/mL) was spotted directly onto a 5 mm circular disc that had been punched from the copolymer grafted nonwoven substrate of Example 38. The spotted substrate was air dried overnight at room temperature. Each disc was loaded with about $2\times10^6$ spores.

Example 54

Individual discs from Examples 52 and 53 were immersed in a beaker containing 500 mL of a peracetic acid (PAA) sterilization solution for six minutes at 50° C. The sterilization solution had a PAA concentration of 1830 ppm and was prepared using Steris S40 Sterilant Concentrate (Steris Corporation, Mentor, Ohio). A total of ten discs were evaluated from each example. Immediately after the exposure time, the discs were removed from the sterilization solution, excess liquid was removed from the discs by gentle shaking, and the discs were transferred to a beaker containing 200 mL of neutralizing solution (5 weight % sodium thiosulfate in sterile, deionized water). The discs were maintained in the neutralization solution for 5 minutes. Each disc was then transferred using sterile forceps to a 15 mL screw-cap conical tube that contained 3 mL of sterilized growth media. The growth media contained L-alanine, peptones, and bro-

TABLE 8

Survival of Test Microorganisms after 5-minute exposure to OPA.

| | Binding Agent | Monomer Units of Copolymer | Percentage of Wells (n = 5) Indicating Outgrowth During Incubation | | |
|---|---|---|---|---|---|
| | | | Day 1 | Day 5 | Day 7 |
| Example 30 | PVA | NVP/GMA/5% IEMAGM | 0% | 0% | 0% |
| Example 31 | PVA | NVP/GMA/2.5% IEMAGM | 0% | 0% | 0% |
| Example 32 | PVA | NVP/GMA/5% DEAEMA | 0% | 0% | 0% |
| Example 33 | PVA | NVP/GMA/2.5% DEAEMA | 0% | 0% | 0% |
| Example 34 | none | NVP/GMA/5% IEMAGM | 0% | 0% | 0% |
| Example 35 | none | NVP/GMA/2.5% IEMAGM | 0% | 0% | 0% |
| Example 36 | none | NVP/GMA/5% DEAEMA | 0% | 0% | 0% |
| Example 37 | none | NVP/GMA/2.5% DEAEMA | 0% | 0% | 0% |
| Example 42 | PVA | NVP/GMA/5% MAPTAC | 0% | 0% | 0% |
| Example 43 | PVA | NVP/GMA/2.5% MAPTAC | 0% | 0% | 0% |
| Example 44 | none | NVP/GMA/5% MAPTAC | 0% | 0% | 0% |
| Example 45 | none | NVP/GMA/2.5% MAPTAC | 0% | 0% | 0% | mocresol purple in water. Each tube was incubated at 58° C. for 7 days. The tubes were checked for outgrowth on days 1, 2, and 7 by visually examining the tubes for color change (purple to yellow) and turbidity of the solution. Yellow solutions with turbidity were positive for outgrowth. Purple solutions without turbidity were negative for outgrowth. Positive control tubes were prepared using discs that had not been exposed to the sterilization solution. Negative control tubes were prepared by not adding a disc to the tube. The results are reported in Table 9. For all positive controls, outgrowth was observed on day 1. Outgrowth was not observed in any of the negative controls for the 7 day period.

TABLE 9

Peracetic Acid Treated Discs

| Disc from Example | Binding Agent | Monomer Units of Copolymer | Percentage of Tubes (n = 10) Indicating Outgrowth During Incubation | | |
|---|---|---|---|---|---|
| | | | Day 1 | Day 2 | Day 7 |
| Example 52 | PVA | NVP/GMA/MAPTAC | 0% | 0% | 0% |
| Example 53 | none | NVP/GMA/MAPTAC | 0% | 0% | 0% |

Example 55

The same procedure as described in Example 39 for preparation of a copolymer grafted nonwoven substrate was followed with the exception that the melt-blown polypropylene microfiber nonwoven substrate had an effective fiber diameter of 9.9 micrometers and a basis weight of 102 grams per square meter. The weight gain by the substrate following grafting was about 220% of the original weight of the substrate.

Example 56

The same procedure as described in Example 39 for preparation of a copolymer grafted nonwoven substrate was followed with the exception that the melt-blown polypropylene microfiber nonwoven substrate had an effective fiber diameter of 8.0 micrometers and a basis weight of 102 grams per square meter. The weight gain by the substrate following grafting was about 266% of the original weight of the substrate.

Example 57

The same procedure as described in Example 39 for preparation of a copolymer grafted nonwoven substrate was followed with the exception that the melt-blown polypropylene microfiber nonwoven substrate had an effective fiber diameter of 6.1 micrometers and a basis weight of 99 grams per square meter). The weight gain by the substrate following grafting was about 263% of the original weight of the substrate.

Example 58

The same procedure as described in Example 39 for preparation of a copolymer grafted nonwoven substrate was followed with the exception that the melt-blown polypropylene microfiber nonwoven substrate had an effective fiber diameter of 3.9 micrometers and a basis weight of 100 grams per square meter. The weight gain by the substrate following grafting was about 272% of the original weight of the substrate.

Example 59

A 2% solution of agarose (melting temperature less than 65° C., catalog number A2790, available from Sigma-Aldrich Corporation) was prepared by adding the agarose to sterile, deionized water and heating in a microwave until dissolved. The agarose solution was then cooled to approximately 40° C. and diluted by adding with a pipet an equal volume of the *Geobacillus stearothermophilus*_spore suspension ($5.4 \times 10^8$ spores/mL). Following the dilution step, the final agarose content of the resulting coating suspension was 10% and the spore concentration was about $2.7 \times 10^8$ spores/mL. Individual aliquots of the coating suspension (10 microliters) were then spotted using a pipet onto 7 mm diameter circular discs that had been punched from the copolymer grafted nonwoven substrates of Examples 55-58. The spotted substrates were air dried overnight at room temperature. Each disc was loaded with about $2.7 \times 10^6$ spores.

Each disc was placed in a tube that contained 9 mL of Butterfield's and the tube was vortexed on the high speed setting for one minute. The disc was removed and the recovered buffer solution was serially diluted in Butterfield's buffer and s plated onto PETRIFILM™ Aerobic Count Plates. The plates were incubated at 56° C. for 24 hours and colonies were counted by visual examination. A total of three discs of each type were analyzed. Based on the number of colonies counted, the percentage of spores washed from each disc was calculated. The mean results are presented in Table 10 with values adjusted based on number of dilutions required.

Example 60

A 10 microliter suspension of *Geobacillus stearothermophilus*_spores ($2.7 \times 10^8$ spores/mL) was prepared. Individual aliquots of the coating suspension (10 microliters) were then spotted using a pipet onto 7 mm diameter circular discs that had been punched from the copolymer grafted nonwoven substrates of Examples 55-58. The spotted substrates were air dried overnight at room temperature. Each disc was loaded with about $2.7 \times 10^6$ spores.

Each disc was placed in a tube that contained 9 mL of Butterfield's buffer and the tube was vortexed on the high speed setting for one minute. The disc was removed and the recovered buffer solution was serially diluted in Butterfield's buffer and plated onto PETRIFILM™ Aerobic Count Plates. The plates were incubated at 56° C. for 24 hours and colonies were counted by visual examination. A total of three discs of each type were analyzed. Based on the number of colonies counted, the percentage of spores washed from each disc was calculated. The mean results are presented in Table 10 with values adjusted based on number of dilutions required.

TABLE 10

| Disc of Example | Effective Fiber Diameter (micrometers) | Binding Agent | Percentage of Spores Removed from the Disc by Washing |
|---|---|---|---|
| 55 | 9.9 | agarose | 0.01 |
| 55 | 9.9 | none | 0.17 |

TABLE 10-continued

| Disc of Example | Effective Fiber Diameter (micrometers) | Binding Agent | Percentage of Spores Removed from the Disc by Washing |
|---|---|---|---|
| 56 | 8.0 | agarose | 0.02 |
| 56 | 8.0 | none | 0.05 |
| 57 | 6.1 | agarose | 0.01 |
| 57 | 6.1 | none | 0.13 |
| 58 | 3.9 | agarose | 0.001 |
| 58 | 3.9 | none | 0.001 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. An article, comprising:
a nonwoven substrate having a copolymer grafted thereto, the copolymer comprising interpolymerized monomer units of
a cationic nitrogen-containing ligand monomer selected from quaternary ammonium-containing and/or guanidinyl-containing ligand monomers;
an amide monomer;
an oxy monomer;
wherein the grafted copolymer comprises:
a. 10 to 50 parts by weight of the cationic nitrogen-containing ligand monomer;
b. 10 to 80 parts by weight of the amide monomer;
c. 10 to 40 parts by weight of the oxy monomer; and
d. 0 to 30 parts by weight of a poly(alkylene oxide) monomer,
wherein the sum of a) to d) is 100 parts by weight; and
a dried coating adhered to the substrate, the coating comprising
an optional water-soluble or water-dispersible polymeric binding agent; and
a plurality of test microorganisms.

2. The article of claim 1, wherein the dried coating further comprises a water-soluble or water-dispersible polymeric binding agent.

3. The article of claim 2, wherein at least a portion of the plurality of test microorganisms is dispersed in the polymeric binding agent.

4. The article of claim 1, wherein the nonwoven substrate comprises meltblown microfibers of a hydrophobic thermoplastic polyolefin.

5. The article of claim 1, wherein the nonwoven substrate has a surface area of 15 to 50 $m^2$ per square meter of nonwoven substrate.

6. The article of claim 1, wherein the nonwoven substrate has a solidity of less than 20%.

7. The article of claim 1, the article can have a weight ratio of copolymer to nonwoven substrate, wherein the weight ratio is about 0.5 to 3 parts copolymer to 1 part nonwoven substrate.

8. The article of claim 1, wherein the plurality of viable test microorganisms consists of about 10 test microorganisms to about $10^8$ test microorganisms.

9. The article of claim 1, wherein the water-soluble or water-dispersible polymeric binding agent comprises poly (alkylene oxide), wherein the poly(alkylene oxide) has a weight average molecular weight of 400 Daltons, 4,000 Daltons, or 20,000 Daltons.

10. The article of claim 1, wherein the quaternary ammonium-containing monomer used to make the copolymer comprises [3-(Methacryloylamino)propyl]trimethylammonium chloride.

11. The article of claim 1, wherein the quaternary ammonium-containing monomer used to make the copolymer comprises [3-(Methacryloylamino)propyl]trimethylammonium chloride, the oxy monomer used to make the copolymer comprises glycidyl methacrylate, and the amide monomer used to make the copolymer comprises N-vinyl pyrrolidone.

12. A process challenge device, comprising:
a body with a hollow channel having a first aperture and a second aperture spaced apart from the first aperture; and
an article fixedly disposed in the hollow channel, the article comprising:
a nonwoven substrate having a copolymer grafted thereto, the copolymer comprising interpolymerized monomer units of
a cationic nitrogen-containing ligand monomer selected from quaternary ammonium-containing and/or guanidinyl-containing ligand monomers;
an amide monomer;
an oxy monomer;
wherein the grafted copolymer comprises:
a. 10 to 50 parts by weight of the cationic nitrogen-containing ligand monomer;
b. 10 to 80 parts by weight of the amide monomer;
c. 10 to 40 parts by weight of the oxy monomer; and
d. 0 to 30 parts by weight of a poly(alkylene oxide) monomer,
wherein the sum of a) to d) is 100 parts by weight; and
a dried coating adhered to the substrate, the coating comprising
an optional water-soluble or water-dispersible polymeric binding agent; and
a plurality of test microorganisms.

13. The process challenge device of claim 12, further comprising a reservoir containing a detection medium, wherein the reservoir is disposed in selective fluid communication with the article.

14. The process challenge device of claim 13, wherein the detection medium comprises a reagent selected from the group consisting of a nutrient that facilitates germination and/or growth of the test microorganisms, an indicator compound facilitates detection of a test microorganism metabolic activity, a neutralizer compound that inhibits an antimicrobial activity of a disinfectant, and a combination of any two or more of the foregoing reagents.

15. The process challenge device of claim 14, wherein the nutrient is selected from the group consisting of serine, proline, arginine, glutamate, asparagine, aspartate, threonine, lipids, fatty acids, potato infusion, yeast extract, malt extract, peptones, dextrose, and a combination of any two or more of the foregoing nutrients.

16. The process challenge device of claim 14, wherein the indicator compound is selected from the group consisting of a chromogenic enzyme substrate, a fluorogenic enzyme substrate, a pH indicator, a redox indicator, a chemiluminescent enzyme substrate, a dye, and a combination of any two or more of the foregoing indicator compounds.

* * * * *